United States Patent
Roszell et al.

(10) Patent No.: US 6,756,059 B2
(45) Date of Patent: Jun. 29, 2004

(54) TOPICAL COMPOSITION, TOPICAL COMPOSITION PRECURSOR, AND METHODS FOR MANUFACTURING AND USING

(75) Inventors: James A. Roszell, Henderson, NV (US); Bruce Jezior, Jupiter, FL (US)

(73) Assignee: Skinvisible Pharmaceuticals, Inc., Las Vegas, NV (US)

( * ) Notice: Subject to any disclaimer, the term of this patent is extended or adjusted under 35 U.S.C. 154(b) by 0 days.

(21) Appl. No.: 09/933,275

(22) Filed: Aug. 20, 2001

(65) Prior Publication Data

US 2003/0044436 A1 Mar. 6, 2003

(51) Int. Cl.[7] .................... A61K 9/10; A61K 9/107; A61K 47/32
(52) U.S. Cl. ................. 424/486; 424/487; 424/400; 514/772.5; 514/772.6; 514/937; 514/944
(58) Field of Search ................ 424/484, 486, 424/487, 78.08, 78.1, 78.11, 78.14, 400; 514/772.5, 772.6, 937, 944

(56) References Cited

U.S. PATENT DOCUMENTS

| 4,035,506 A | 7/1977 | Lucas et al. ............... 424/303 |
| 4,301,145 A | 11/1981 | Cestari ..................... 424/80 |

(List continued on next page.)

FOREIGN PATENT DOCUMENTS

| EP | 640352 | 3/1995 |
| EP | 747062 | 12/1996 |
| EP | 391741 | 4/1998 |
| JP | 10095714 A | 9/1996 |

OTHER PUBLICATIONS

Bradley, C. et al., "Noninvasive Transdermal Chemical Collection", *Skin Pharmacol*, pp. 218–226 (1990).

Hasirei, V., "Synthesis and characterization of PVNO and PVNO–PVP hydrogels", *Biomaterials*, vol. 2, No. 1, 7 pages (Jan. 1981).

Material Safety Data Sheet, Gantrez S–97 BF Solution, ISP Technologies, Inc., 6 pages (Apr. 7, 1994).

Material Safety Data Sheet, Ganez V–216, ISP Technologies, Inc., pages 5 pages (Sep. 16, 1994).

Material Safety Data Sheet, Ganex V–220, ISP Technologies, Inc., 5 pages (Oct. 7, 1998).

Nair, P. et al., "Studies on the effect of degree of hydrophilicity on tissue response of polyurethane interpenetrating polymer networks", *Biomaterials*, vol. 13, No. 8, pp. 536–542 (1992).

Shinichi, N. et al., "Hair treatment agent—includes specific high molecular copolymer compounds by which skin layer is made to form on hair surface", *Derwent Abstract* (ACC#1998–280363; Week# 199825) (1999).

Tiller et al., "Designing surfaces that kill bacteria on contact", http://www/pnas.org/cgi/content/abstract/98/11/5981, PNAS Online, 2 pages (May 22, 2001).

*Primary Examiner*—Edward J. Webman
(74) *Attorney, Agent, or Firm*—Merchant & Gould P.C.

(57) ABSTRACT

A tropical composition is provided. The topical composition can be prepared by diluting a topical composition precursor with water and adding additional components, if desired. The topical composition precursor can be prepared by melt processing a hydrophobic polymer composition that includes repeating pyrrolidone/alkylene groups wherein the alkylene groups contain at least 10 carbon atoms, and a hydrophilic polymer composition including repeating carboxylic groups and/or repeating hydroxyl groups. A topical composition precursor and methods for manufacturing and using a topical composition are provided by the invention.

26 Claims, 14 Drawing Sheets

Change in % Free COOH of Maleic Acid/ Methylvinylether Copolymer as a Function of % Polyvinylpyrrolidone with 1-Eicosene

U.S. PATENT DOCUMENTS

| Patent No. | | Date | Inventor(s) | Class |
|---|---|---|---|---|
| 4,448,906 | A | 5/1984 | Deinet et al. | 523/722 |
| 4,500,338 | A | 2/1985 | Young et al. | 71/67 |
| 4,507,279 | A | 3/1985 | Okuyama et al. | 424/63 |
| 4,645,794 | A | 2/1987 | Davis et al. | 525/61 |
| 4,671,957 | A | 6/1987 | Holtshousen | 424/80 |
| 4,803,066 | A | 2/1989 | Edwards | 424/732 |
| 4,810,489 | A | 3/1989 | Murray et al. | 424/59 |
| 4,840,687 | A * | 6/1989 | Forsberg et al. | |
| 4,897,259 | A | 1/1990 | Murray et al. | 514/938 |
| 4,971,800 | A | 11/1990 | Chess et al. | 424/449 |
| 5,019,604 | A | 5/1991 | Lemole | 523/105 |
| 5,045,317 | A | 9/1991 | Chess et al. | 424/401 |
| 5,051,260 | A | 9/1991 | Chess et al. | 424/449 |
| 5,055,303 | A | 10/1991 | Riley, Jr. | 424/436 |
| 5,082,656 | A | 1/1992 | Hui et al. | 514/24 |
| 5,126,136 | A | 6/1992 | Merat et al. | 424/401 |
| 5,155,199 | A | 10/1992 | Hayashi | 528/65 |
| 5,232,691 | A | 8/1993 | Lemole | 424/78.02 |
| 5,266,329 | A | 11/1993 | Riley, Jr. | 424/430 |
| 5,320,838 | A | 6/1994 | Woller | 424/78.02 |
| 5,336,305 | A | 8/1994 | Staats | 106/18.32 |
| 5,370,876 | A | 12/1994 | Noll et al. | 424/407 |
| 5,417,968 | A | 5/1995 | Staats | 424/78.07 |
| 5,431,756 | A * | 7/1995 | Kosowski et al. | |
| 5,597,849 | A | 1/1997 | McGinity et al. | 514/648 |
| 5,605,676 | A | 2/1997 | Gaffar et al. | 424/49 |
| 5,607,979 | A | 3/1997 | McCreery | 514/759 |
| 5,622,993 | A | 4/1997 | McGinity et al. | 514/626 |
| 5,658,559 | A | 8/1997 | Smith | 424/78.02 |
| 5,707,612 | A | 1/1998 | Zofchak et al. | 424/69 |
| 5,721,306 | A | 2/1998 | Tsipursky et al. | 524/449 |
| 5,725,844 | A | 3/1998 | Gers-Barlag et al. | 424/59 |
| 5,725,875 | A | 3/1998 | Noll et al. | 424/445 |
| 5,730,966 | A | 3/1998 | Torgerson et al. | 424/70.11 |
| 5,747,022 | A | 5/1998 | Slavtcheff | 424/78.03 |
| 5,807,957 | A | 9/1998 | Samour et al. | 528/49 |
| 5,834,538 | A | 11/1998 | deHullu et al. | 524/22 |
| 5,874,074 | A | 2/1999 | Smith | 424/78.02 |
| 5,891,470 | A | 4/1999 | Rinaldi et al. | 424/451 |
| 5,906,822 | A | 5/1999 | Samour et al. | 424/401 |
| 5,911,980 | A | 6/1999 | Samour et al. | 424/70.17 |
| 5,939,453 | A | 8/1999 | Heller et al. | 514/452 |
| 5,942,545 | A | 8/1999 | Samour et al. | 514/573 |
| 5,955,109 | A | 9/1999 | Won et al. | 424/501 |
| 5,968,543 | A | 10/1999 | Heller et al. | 424/425 |
| 5,968,919 | A | 10/1999 | Samour et al. | 514/177 |
| 5,976,566 | A | 11/1999 | Samour et al. | 424/449 |
| 5,980,876 | A | 11/1999 | Peffly | 424/70.12 |
| 6,096,344 | A | 8/2000 | Liu et al. | 424/501 |
| 6,582,683 | B2 | 6/2003 | Jezior | |

* cited by examiner

US 6,756,059 B2

TOPICAL COMPOSITION, TOPICAL COMPOSITION PRECURSOR, AND METHODS FOR MANUFACTURING AND USING

FIELD OF THE INVENTION

The invention relates to a topical composition, a topical composition precursor, and methods for manufacturing and using the topical composition and the composition precursor.

BACKGROUND OF THE INVENTION

Naturally occurring and synthetic polymers have been used in pharmaceutical and cosmetic preparations for several decades. Polymers that have been used in pharmaceutical and cosmetic preparations include hydrophilic polymers, hydrophobic polymers, and polymers having hydrophilic and hydrophobic properties. Hydrophilic polymers are often used as thickeners and/or film formers. Hydrophobic polymers are often used because of their ability to hold active ingredients and to bind to skin.

Compositions have been developed for enhancing the cutaneous penetration of topically or transdermally delivered pharmacologically active agents. For example, see U.S. Pat. Nos. 5,045,317; 5,051,260; and 4,971,800.

SUMMARY OF THE INVENTION

A topical composition, a topical composition precursor, and methods for manufacturing and using a topical composition and a topical composition precursor are provided by the invention. The topical composition can be referred to as a "delivery system" when it is used to promote the delivery of active ingredients to skin tissue. When provided as a use solution, the topical composition has an ability to adhere or bind to skin tissue and thereby hold active ingredients in proximity to skin tissue. In addition, the topical composition has an ability to hold or contain active ingredients so that the active ingredients can be made available to skin tissue when the topical composition is applied to skin tissue. Active ingredients that can be used include natural and synthetic substances that produce a desired effect when placed on skin tissue and may include medicines or drugs or other substances intended for the diagnosis, cure, mitigation, treatment, or prevention of a disease or condition, and may include substances that may be characterized as protectants, repellants, and moisturizers.

The topical composition precursor of the invention can be provided as a result of melt processing a hydrophobic polymer composition and a hydrophilic polymer composition in the presence of less than about 1 wt. % water. The hydrophobic polymer composition includes a poly(vinylpyrrolidone/alkylene) polymer wherein the alkylene group contains at least about 10 carbon atoms. The hydrophilic polymer composition includes at least one of a hydrophilic polymer comprising repeating carboxylic acid groups and/or repeating hydroxyl groups. Exemplary hydrophilic polymers include polyacrylic acid having a weight average molecular weight of at least about 50,000 and exhibiting less than 1% cross-linking, poly(maleic acid/methylvinylether) copolymer having a weight average molecular weight of at least about 50,000, starch, derivatives of starch, cellulose, derivatives of cellulose, carboxymethyl cellulose, polyvinyl alcohol, cyclodextrins, dextrans, and mixtures thereof. The hydrophilic polymer composition can include polyacrylic acid having a weight average molecular weight of between about 50,000 and about 4,000,000, and exhibits less than 1% cross-linking and/or poly(maleic acid/methylvinylether) copolymer having a weight average molecular weight of between about 50,000 and about 4,000,000.

The hydrophobic polymer composition can include a mixture of different poly(vinylpyrrolidone/alkylene) polymers. When the hydrophobic polymer composition contains a mixture of two different poly(vinylpyrrolidone/alkylene) polymers, the first poly(vinylpyrrolidone/alkylene) polymer can be provided at a concentration of between about 5 wt. % and about 54 wt. %, based on the weight of the hydrophobic polymer composition. In addition, the second poly(vinylpyrrolidone/alkylene) polymer can be provided at a concentration of between about 46 wt. % and about 95 wt. %, based on the weight of the hydrophobic polymer composition. Exemplary poly(vinylpyrrolidone/alkylene) polymers include poly(vinylpyrrolidone/1-eicosene) polymer and poly(vinylpyrrolidone/hexadecene).

The topical composition precursor can be formed by mixing the hydrophobic polymer composition and the hydrophilic polymer composition in a melt and providing a functional group parity between the pyrrolidone groups of the hydrophobic polymer composition and the combination of carboxylic acid groups and/or hydroxyl groups of the hydrophilic polymer composition that is between about 1:1 and about 5:1, and can be between about 1.5:1 and about 3:1. For certain compositions, it is expected that this functional group parity of the hydrophobic polymer composition to the hydrophilic polymer composition will result in a topical composition precursor containing about 72 wt. % to about 98 wt. % hydrophobic polymer composition and about 2 wt. % to about 25 wt. % hydrophilic polymer composition, based on the total weight of the topical composition precursor.

A topical composition is provided according to the invention. The topical composition can include the topical composition precursor and can include a result of diluting the topical composition precursor with water. The topical composition preferably includes a result of hydrating the topical composition precursor with water to provide at least about 30 wt. % water. The topical composition can be characterized as a concentrate if it contains between about 30 wt. % and about 70 wt. % water based on the weight of the topical composition. It is expected that the concentrate will be provided with a water concentration of between about 30 wt. % and about 45 wt. % to reduce costs associated with shipping water. When the topical composition is provided as a use solution for application to skin tissue, it is expected that the composition will contain at least about 70 wt. % water and can include between about 70 wt. % and about 96 wt. % water, based on the weight of the topical composition.

The topical composition can include active ingredients such as antimicrobials, antifungals, anti-inflammatory agents, anti-viral agents, drugs, sunscreens, vitamins, alpha-hydroxy acids, surfactants, dyes, fragrances and pigments.

The topical composition can include a surfactant or a mixture of surfactants to enhance the stability of the topical composition and/or to enhance the rate of release of active ingredients. Exemplary surfactants that can be used according to the invention include nonionic surfactants, anionic surfactants, cationic surfactants, amphoteric surfactants, and mixtures thereof. Exemplary nonionic surfactants that can be used according to the invention include ethoxylated surfactants, propoxylated surfactants, and ethoxylated-propoxylated surfactants. An exemplary ethoxylated surfactant includes nonylphenol ethoxylate having about nine ethylene oxide repeating groups. The surfactant component can be incorporated into the topical composition in an amount sufficient to provide the desired stability and the desirable rate of release of active ingredients. In most applications, it is expected that the surfactant will be provided in an amount of up to about 5 wt. %, and will more likely be provided in an amount of between about 0.5 wt. % and about 5 wt. %.

A method for manufacturing a topical composition is provided according to the invention. The method includes a step of melt processing a mixture of a hydrophobic polymer composition and a hydrophilic polymer composition to provide a topical composition precursor, and diluting the topical composition precursor to provide a concentrate having a water concentration of at least about 30 wt. %, based on the weight of the topical composition. The step of melt processing preferably includes mixing the hydrophobic polymer composition and the hydrophilic polymer composition at a temperature of greater than 50° C., and more preferably greater than about 125° C. The step of melt processing preferably includes mixing the hydrophobic polymer composition and the hydrophilic polymer composition at a water concentration of less than about 1 wt. %.

A method for using a topical composition is provided according to the invention. The method includes applying the topical composition to skin tissue.

DETAILED DESCRIPTION OF THE INVENTION

Figure 1:
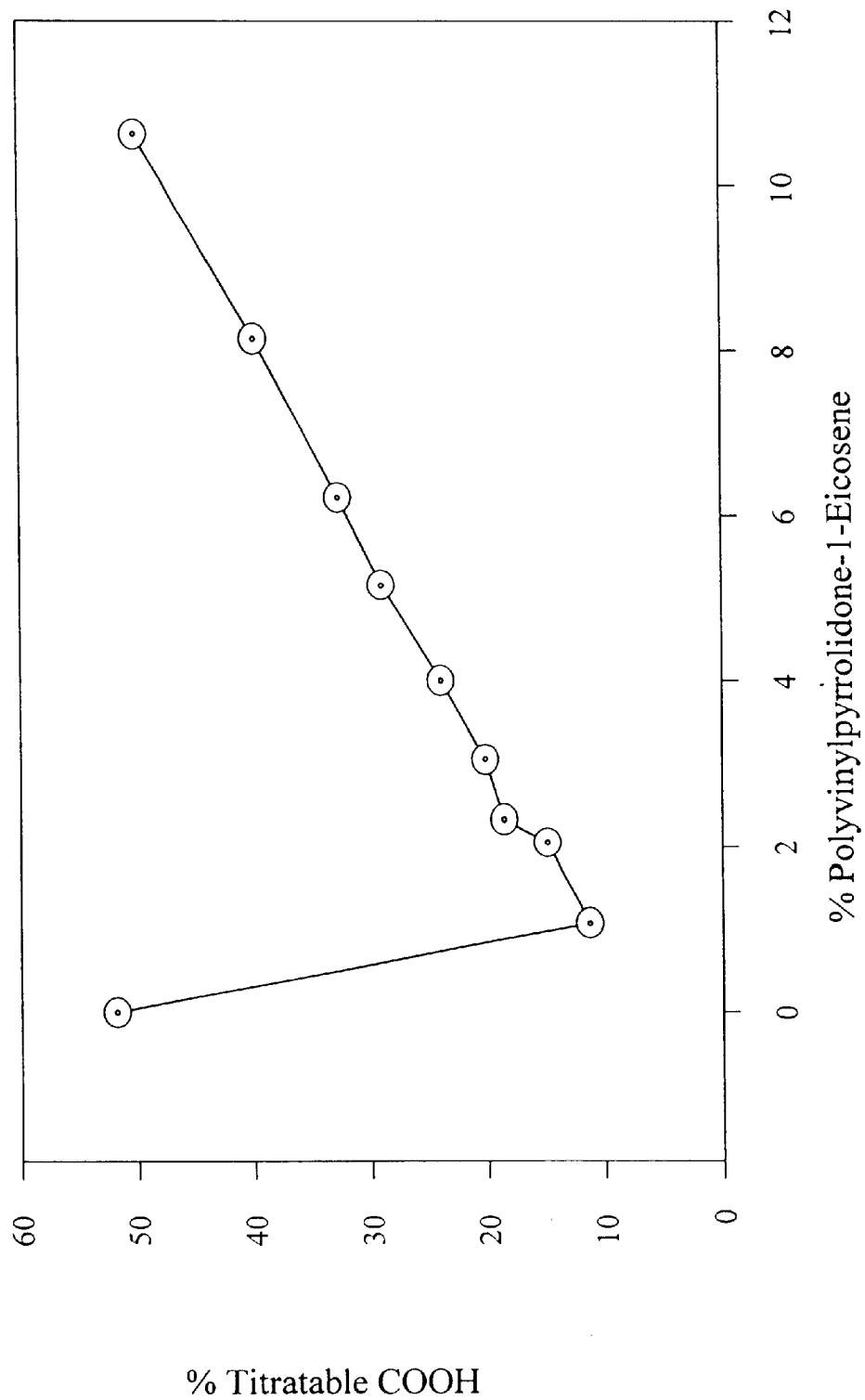
FIG. 1 is a graph showing the change in percent free COOH of maleic acid/methylvinylether copolymer as a function of percent polyvinylpyrrolidone with 1-eicosene.

A topical composition and a topical composition precursor are provided by the invention. The topical composition precursor refers to a relatively anhydrous composition that is used to form the topical composition use solution or working solution. The topical composition use solution or working solution refers to the composition intended to be applied directly to skin tissue. It should be understood that the phrase "topical composition" refers to any composition that includes the topical composition precursor as a component or that can be formed from the topical composition precursor, and may be provided in the form of a precursor, a concentrate, a use solution, or an intermediate in the production of a topical composition use solution.

The topical composition can be referred to as a delivery system when it includes an active ingredient for delivery to skin tissue. The topical composition according to the invention is advantageous because of its ability to bind or adhere to skin tissue for a length of time and because of its ability to hold or contain active ingredients within the composition to allow for delivery of the active ingredients to skin tissue. It is expected that the topical composition is able to adhere or bind to skin tissue for at least about four hours and holds the active ingredients contained therein in proximity to skin tissue for that length of time to allow for delivery of the active ingredients to the skin tissue. In general, it is expected that the topical composition will bind or adhere to skin tissue for at least four hours even after several applications of washing and scrubbing of the skin tissue. It is expected that the natural exfoliation of the skin will cause the removal of most of the topical composition from the skin tissue.

The topical composition precursor can be prepared by melt processing a hydrophobic polymer composition and a hydrophilic polymer composition to provide an interaction between the hydrophobic polymer composition and the hydrophilic polymer composition. It should be understood that the phrase "melt processing" refers to mixing the hydrophobic polymer composition and the hydrophilic polymer composition under conditions that provide that the hydrophobic polymer component of the hydrophobic polymer composition and the hydrophilic polymer component of the hydrophilic polymer composition are in a liquid state so that they sufficiently mix. When the polymers are sufficiently mixed, it is believed that an interaction forms between the hydrophobic polymer component and the hydrophilic polymer component. The melt processing temperature is preferably at least about 50° C. and more preferably at least about 125° C. to generate this interaction.

It is believed the interaction exhibited between the hydrophobic polymer component and the hydrophilic polymer component is a type of complex formation reaction, and that the complexes, once formed, are stable in water at temperatures up to 65° C. and at a pH range of 3.0 to 9.0. By stable, it is meant that the complexes do not favor disassociation. It is believed that this interaction provides the topical composition with an ability to bind or hold onto hydrophobic active ingredients that are emulsified in water, and provides the topical composition with an ability to bind to skin and/or substrates of predominantly hydrophobic character.

Hydrophobic Polymer Composition

The hydrophobic polymer composition that can be used according to the invention includes repeating pyrrolidone/ alkylene groups. Exemplary polymers that have repeating pyrrolidone/alkylene groups include poly(vinylpyrrolidone/alkylene). Poly(vinylpyrrolidone/alkylene) polymers include those polymers obtained by a polymerizing alkylene substituted vinylpyrrolidone. The polymers can be represented by the following general formula:

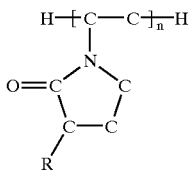

wherein R represents a carbon chain substitute such as an alkylene group and n represents the number of repeating units. The R group is preferably sufficiently long so that the polymer remains relatively water insoluble and should not be too long so that the polymer is difficult to melt process. Preferably, the alkylene group contains a length of at least about 10 carbon atoms and contains no more than about 25 carbon atoms. Preferably, the alkylene group contains between about 14 carbon atoms and about 22 carbon atoms, and more preferably between about 15 carbon atoms and about 19 carbon atoms.

The poly(vinylpyrrolidone/alkylene) polymers that can be used according to the invention preferably have a molecular weight that is sufficiently high so that the polymer maintains its water insolubility but the molecular weight should not be so high that it becomes difficult to melt process the polymer. Preferably, the weight average molecular weight of the poly(vinylpyrrolidone/alkylene) polymer is between about 3,000 and about 400,000. Another way to characterize the size of the poly(vinylpyrrolidone/alkylene) polymer is by the number of repeating units (n). In the case of a poly(vinylpyrrolidone/alkylene) polymer having a weight average molecular weight of between about 6,000 and about 30,000, the poly(vinylpyrrolidone/alkylene) polymer has between about 20 and about 80 repeating units, and more preferably between about 30 and about 50 repeating units. It should be understood that repeating units refer to the residues of vinylpyrrolidone/alkylene groups.

Preferred poly(vinylpyrrolidone/alkylene) polymers that can be used according to the invention include poly(vinylpyrrolidone/1-eicosene) and poly(vinylpyrrolidone/hexadecene). Poly(vinylpyrrolidone/1-eicosene) can be referred to as PVPE and is commonly used in pharmaceutical and cosmetic preparations. A preferred form of PVPE for use according to the invention includes about 43 to 44 repeating units in length and has a weight average molecular weight of about 17,000 and can be characterized as a paraffin-like solid. This particular PVPE is highly insoluble in water, and has an extremely low oral toxicity ($LD_{50}$>17000 mg/kg) and exhibits no demonstrable dermal toxicity. Poly(vinylpyrrolidone/1-hexadecene) can be referred to as PVPH. A preferred form of PVPH is available as a viscous yellow liquid that is insoluble in water and has a low oral toxicity ($LD_{50}$>64000 mg/kg), has about 39 to 40 repeating units, a molecular weight of about 1,400, and exhibits no demonstrable dermal toxicity.

PVPE and PVPH differ in the length of the hydrocarbon side chain, and are used extensively in the skin care industry, usually in concentrations of less than 1% by weight, because of their ability to bind to skin. Because the skin care industry generally prefers to apply actives to skin using a water-based composition, the use of PVPE and PVPH often requires solvents, surfactants, and emulsifiers to stabilize these polymers in a water emulsion. However, many of the solvents, surfactants and emulsifiers used to stabilize PVPE and PVPH in a water emulsion lack the low dermal toxicities of PVPE and PVPH. PVPE and PVPH by themselves lack a cosmetically elegant appeal when applied directly to the skin. They tend to be sticky and greasy.

The hydrophobic polymer composition used according to the invention is preferably provided as a mixture of different poly(vinylpyrrolidone/alkylene) polymers. The mixtures of different poly(vinylpyrrolidone/alkylene) polymers preferably include at least 5 wt. % of a first poly(vinylpyrrolidone/alkylene) polymer based on the weight of the hydrophobic polymer composition. The hydrophobic polymer composition preferably includes between about 5 wt. % and about 54 wt. % of the first poly(vinylpyrrolidone/alkylene) polymer. The second poly(vinylpyrrolidone/alkylene) polymer is preferably provided in an amount of at least about 46 wt. % and preferably in a range of between about 46 wt. % and 95 wt. %. For a hydrophobic polymer composition containing a first poly(vinylpyrrolidone/alkylene) polymer and a second poly(vinylpyrrolidone/alkylene) polymer, the mole ratio of the first polymer to the second polymer is preferably between about 1:22 and about 1:1. In general, when the hydrophobic polymer composition contains a mixture of different poly(vinylpyrrolidone/alkylene) polymers, it is preferable to provide at least one of the poly(vinylpyrrolidone/alkylene) polymers in an amount that provides improved properties to the topical composition compared to a topical composition having a hydrophobic polymer composition containing a single poly(vinylpyrrolidone/alkylene) polymer.

When the hydrophobic polymer composition is provided as a mixture of PVPH and PVPE, it is preferable that the PVPH is provided in the range of between about 46 wt. % to about 95 wt. % and the PVPE is provided in the range of between about 5 wt. % and about 65 wt. %, based upon the weight of the hydrophobic polymer composition.

Hydrophilic Polymer Composition The hydrophilic polymer composition that can be used according to the invention includes at least one hydrophilic polymer and may include a mixture of hydrophilic polymers. The hydrophilic polymers that can be used according to the invention include polymers having repeating carboxylic acid groups and/or hydroxyl groups. Preferred hydrophilic polymers that can be used according to the invention include polyacrylic acid polymers and poly(maleic acid/methylvinylether) copolymers.

Polyacrylic acid polymers that can be used according to the invention preferably have a weight average molecular weight of at least about 50,000, and more preferably between about 50,000 and about 4,000,000. In addition, the polyacrylic acid polymers preferably have a level of crosslinking that is less than about 1%. A general structural representation of polyacrylic acid polymers is shown below:

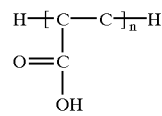

wherein n is the number of repeating units and is preferably between about 1,000 and about 20,000.

Poly(maleic acid/methylvinylether) copolymers that can be used according to the invention preferably have a weight average molecular weight of at least about 50,000, and preferably between about 50,000 and about 4,000,000. The weight average molecular weight is more preferably between about 70,000 and 2,500,000. A general structural representation of poly(maleic acid/methylvinylether) copolymers is shown below:

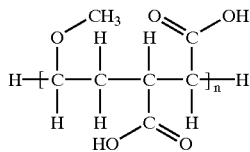

wherein n is the number of repeating units and is preferably between about 200 and about 20,000.

Additional hydrophilic polymers that can be used according to the invention include starch, derivatives of starch, polyvinyl alcohol, cellulose, derivatives of cellulose, carboxymethyl cellulose, cyclodextrins, and dextrans. Exemplary starches include amylopectin and polyglucose. The weight average molecular weight of the hydrophilic polymers is preferably sufficient to provide solubility in water but not too high to become difficult to process. Starches that can be used according to the invention preferably have a weight average molecular weight of between about 50,000 and about 20,000,000. A derivative of starch that can be used according to the invention includes partially hydrolized starch. Cellulose that can be used according to the invention preferably has a weight average molecular weight of between about 50,000 and about 15,000,000. Polyglucose that can be used according to the invention can be characterized as low fraction polyglucose having a weight average molecular weight of between about 60,000 and about 90,000, and high fraction polyglucose having a weight average molecular weight of between about 90,000 and about 300,000. An exemplary low fraction polyglucose material that can be used according to the invention is available under the name Dextran-70. In general, this type of polyglucose has all alpha 1–6 linkages. Starch derivatives that can be used according to the invention include those starch derivatives having alpha 1–4 linkages. An example of this type of starch derivative includes cyclodextrins. Preferred cyclodextrins that can be used according to the invention are those that act to provide a cavity within the molecule large enough to contain components desirable for topical applications. Preferably, the cyclodextrins that can be used according to the invention have a molecular weight of between about 900 and about 1,400. Polyvinyl alcohols that can be used according to the invention preferably have a weight average molecular weight of between about 50,000 and about 200,000.

Exemplary hydrophilic polymers that can be used according to the invention include those polymers having the following melting temperature range and the following maximum temperature range beyond which it is expected decomposition of the polymer will occur. Exemplary poly (maleic acid/methylvinylether) copolymers that can be used include those having a melting temperature range of between about 60° C. and about 65° C. and a maximum temperature range of between about 80° C. and about 90° C. Exemplary polyacrylic acid polymers that can be used include those having a melting temperature range of between about 65° C. and about 70° C. and a maximum temperature range of between about 80° C. and about 90° C. Exemplary carboxymethyl cellulose polymers that can be used include those having a melting temperature range of between about 55° C. and about 60° C. and a maximum temperature range of between about 75° C. and about 80° C. Exemplary polyvinyl alcohol polymers that can be used include those having a melting temperature range of between about 50° C. and about 55° C. and a maximum temperature range of between about 65° C. and about 70° C. Exemplary starches that can be used include those having a melting temperature range of between about 40° C. and about 45° C. and a maximum temperature range of between about 50° C. and about 55° C. Exemplary dextrans that can be used include those having a melting temperature range of between about 37° C. and about 40° C. and a maximum temperature range of between about 45° C. and about 50° C. Exemplary β-cyclodextrins that can be used according to the invention include those having a melting temperature range of between about 40° C. and about 45° C. and a maximum temperature range of between about 65° C. and about 70° C.

Processing

The hydrophobic polymer composition and the hydrophilic polymer composition are preferably combined and heated to at least about 50° C. to provide a polymer melt. The composition is preferably heated to at least about 125° C. under mixing to form complexes between the hydrophobic and hydrophilic polymers.

The complex formation step is preferably carried out in a relatively anhydrous environment. That is, the amount of water provided in the composition during the complex formation step is preferably less than about 1 wt. %. Once the desired level of complex formation has occurred, the composition can be hydrated with water.

The hydrophobic polymer composition and the hydrophilic polymer composition are preferably mixed together in amounts sufficient to provide a ratio of pyrrolidone groups to the combination of carboxylic acid groups and hydroxyl groups of between about 1:1 and about 5:1. The ratio of the structures causing the observed interaction between the hydrophobic polymer composition and the hydrophilic polymer composition can be referred to as "functional group parity." Preferably, the ratio of pyrrolidone groups to the combination of carboxylic acid groups and hydroxyl groups is between about 1.5:1 and about 3:1. In order to drive the complex formation reaction, it is desirable to provide an imbalance between the two types of groups. Accordingly, it is generally desirable to provide more of the pyrrolidone groups than the combination of carboxylic groups and the hydroxyl groups. It should be understood that the reference to a "combination of carboxylic groups and hydroxyl groups" refers to the total amount of carboxylic groups and hydroxyl groups present but does not require the presence of both carboxylic groups and hydroxyl groups. For example, the value of the combination of carboxylic groups and hydroxyl groups can be determined for a composition that contains only carboxylic groups. Similarly, the value can be determined for a composition that contains only hydroxyl groups.

During the complex formation step, the amounts of hydrophobic polymer composition and hydrophilic polymer composition can be characterized on a weight percent basis. Preferably, about 2 wt. % to about 28 wt. % hydrophilic polymer composition and about 72 wt. % to about 98 wt. % hydrophobic polymer composition are combined to provide for complex formation. Preferably, about 8 wt. % to about 25 wt. % hydrophilic polymer composition and about 72 wt. % to about 95 wt. % hydrophobic polymer composition are combined to form the complex. During the complex formation step, the amount of water available in the composition is preferably less than about 1 wt. %. Although the complex forming composition can be relatively anhydrous, it is expected that the amount of water will be between about 0.3 wt. % and about 1.0 wt. %.

Once the hydrophobic polymers and the hydrophilic polymers have sufficiently reacted or interacted to form complexes, it is desirable to add water to the composition to provide a stable aqueous composition that can be relatively easily further hydrated. The stable aqueous composition that can be easily diluted further with water to form the use solution can be referred to as the concentrate. It is generally desirable to hydrate the composition to a water content that provides a relatively stable composition and that allows for water to be added at a later date without much difficulty. Although water can be added to the composition to a level equivalent to the level of the topical composition use solution, it is desirable to minimize the amount of water to avoid having to ship water. Shipping excess water is expected to add cost to the composition. In addition, it has been found that the first hydration of the topical composition precursor is the most difficult hydration step because of the need to control the conditions of hydration. After the first hydration to a water content of at least about 30 wt. %, it is expected that further hydrations to higher water contents are relatively easy and can be accomplished by simply mixing the composition with water. Accordingly, the amount of water provided in the composition when made available as a concentrate for shipment is preferably between about 30 wt. % and about 45 wt. %. When the composition includes about 30 wt. % to about 45 wt. % water, it is expected that the composition will include between about 3 wt. % and about 10 wt. % hydrophilic polymer composition and between about 30 wt. % and about 50 wt. % hydrophobic polymer composition.

Water is added to the relatively anhydrous composition by mixing water and the relatively anhydrous composition at a temperature and for a time sufficient to allow the composition to become hydrated without losing significant amounts of interaction between the hydrophobic polymer composition and the hydrophilic polymer composition. In general, the relatively anhydrous composition is hydrated by heating to at least 60° C. and adding water while mixing. Preferably, the composition is heated to at least about 65° C. and more preferably at least about 70° C. A preferred temperature range is about 65° C. to about 80° C.

The relatively anhydrous composition can be referred to as the topical composition precursor. The topical composition having a water concentration of between about 30 wt. % and about 95 wt. % can be referred to as the concentrate. It is expected that the concentrate will be made available to manufacturers of topical compositions. In addition, it is expected that the concentrate made available to manufacturers of topical compositions will have a water concentration of between about 30 wt. % and about 45 wt. %. The manufacturers of topical compositions will either further hydrate the composition or use it as it is made available to them. In most applications, it is expected that the topical composition manufacturers will dilute the topical composition concentrate to the desired concentration of water and polymer components, and then use that composition as a component of the topical composition.

Additional Components

The topical composition use solution is preferably prepared by mixing the topical composition concentrate with additional components for the formation of the use solution. Components that can be incorporated into the composition for forming the use solution include those components normally encountered in the topical composition industry. Exemplary components include antimicrobial agents, antifungal agents, anti-inflammatory agents, anti-viral agents, sunscreens, vitamins, α-hydroxy acids, surfactants, pigments, and dyes. Components that are generally best suited for the composition of the invention include those active ingredients that can be characterized as hydrophobic, neutral polar such as alcohols, and acidic.

Exemplary antimicrobial agents or biocidal agents that can be used according to the invention include those agents that are known to those of skill in the art, including quaternary ammonium compounds and peroxygen compounds such as peroxy acids. Biocidal agents that can be used include chlorinated diphenyl ethers such as those available under the tradename Triclosan®. When used, this agent can be present at a concentration of about 0.9 to about 1.1 wt-%, more preferably about 1.0 wt-%. Tricosan® gives a broad spectrum of pathogenic coverage and has a long history of safe usage with a benign toxicological profile. An exemplary natural antimicrobial agent that can be used for treating inflammation and psoriasis includes silver.

Exemplary antifungal agents that can be used include sulconazole, naftifine, morpholines, allylamines, triazoles, clotrimazole and miconazole nitrate.

The topical composition can also be used as long lasting carriers for insecticides. A number of insecticides are known in the art as safe for human use, including citronella. Preferred insecticides include N,N'-diethyl-3-methylbenzamide, commonly known as DEET.

Exemplary sunscreen agents that can be used include FSDA approved materials such as aminobenzoic acid-PABA, cinoxate, diethanolamine methoxycinnamate, digalloyl trioleate, dioxybenzone, ethyl 4[bis(hydroxypropyl)] aminobenzoate, glyceryl aminobenzoate, homosalate, lawsone with dihydroxyacetone, mentyl anthranilate, octocrylene, octyl methoxycinnamate, octyl salicylate, oxybenzone, benzophenone, padimate, phenylbenzimidazole sulfonic acid, red petrolaum, sulisobenzone, titanium dioxide, trolamine salicylate, and combinations of the above. Preferred sunscreen materials include a mixture of octyl methoxycinnamate and benzophenone.

Exemplary active ingredients that can be used in the topical composition include benzalkonium chloride (antimicrobial), benzophenone (sunscreen), glycerin (skin moisturizer), iodine (antimicrobial), vitamin A (skin healing), vitamin D and D2 (skin healing), aloe (skin healing), octyl methoxycinnamate (sunscreen), anise oil, garlic oil, hydrocortisone (anti-inflammatory), salicylic acid (acne preparation), DEET (insect repellent), phenol-TEA complex (antimicrobial), clotrimazole (antifungal), and miconazole nitrate (antifungal).

Active ingredients that can be used in the topical composition according to the invention include natural and synthetic drugs. Exemplary drugs that can be used for topical applications include those listed in U.S. Pharmacopeia and National Formulary, The United States Pharmacopeial Convention, Inc., Rockville, Md. and Physician's Desk Reference, Medical Economics Co., Inc., Oradell, N.J.

Surfactants can be incorporated into the topical composition to provide controlled release of active ingredient or other component in the topical composition. It is expected that the amount of surfactant and the type of surfactant can be adjusted to increase or decrease the release rate. In the case where an active ingredient or other component desired to be released is relatively more hydrophobic, it is expected that by increasing the surfactant concentration, an equilibrium shift favors the aqueous phase and promotes a faster release of the ingredient.

Surfactants that can be incorporated into the topical composition according to the invention include nonionic surfactants, cationic surfactants, anionic surfactants, and amphoteric surfactants, and mixtures thereof. It may be desirable to use surfactants when they have a tendency to increase the emulsion stability and/or to promote the release of active ingredients. That is, surfactants can be used to increase the water solubility of the polymers of the topical composition and/or the surfactants can be used to decrease the binding of the active ingredients to the polymers of the topical composition.

Nonionic surfactants that can be used according to the invention include ethoxylated, propoxylated, ethoxylated-propoxylated surfactants, and mixtures thereof. An exemplary nonionic surfactant that can be use according to the invention includes nonylphenol ethoxylate having nine ethylene oxide groups and is available under the name Nonoxynol-9. When nonylphenol ethoxylate is used according to the invention, it is preferably provided in an amount of up to 5 wt. %, and can be provided at a concentration of between about 0.5 wt. % and about 5 wt. %, and at a concentration of between about 0.6 wt. % and about 1 wt. %. As discussed previously, the amount of the surfactant can be adjusted to provide desired emulsion stability and to effect the rate of release of active ingredient.

The use of surfactants for releasing active ingredients from the topical composition is believed to be most useful with active ingredients that can be characterized as hydrophobic.

Anionic surfactants that can be used according to the invention includes salts of carboxylic (soaps) and sulfonate salts (detergents). Cationic surfactants that can be used according to the invention include amides such as cocoamide. One concern with the use of anionic surfactants, cationic surfactants, and amphoteric surfactants relates to the potential destabilization of a emulsions as a result of the presence of salts. Accordingly, it may be desirable to use anionic surfactants, cationic surfactants, and amphoteric surfactants at sufficiently low levels to reduce this destabilizing effect. It is expected that these surfactants will be used at lower levels than nonionic surfactants. In addition, the positive charge of the cationic surfactants and the amphoteric surfactants can have an affect of forming insoluable complexes with portions of the hydrophilic polymer composition.

When surfactants are used according to the invention, it is generally desirable to use the surfactant or mixture of surfactants in an amount that provides a desired level of emulsion stability and provides a desired rate of release of active ingredients. It is expected that in most applications, the surfactant or mixture of surfactants will be provided at a concentration of up to about 5 wt. %, and can be provided in a range of 0.5 wt. % and 5 wt. %, and within a narrower range of about 0.6 wt. % and about 1 wt. %.

Although the topical composition has been described as a composition that includes additional components, it should be understood that the topical composition can be used as a replacement for chemicals or additives used in presently available topical compositions that are on the market. That is, certain ingredients of existing topical compositions can be replaced by the topical composition of the invention. For example, may commercially available topical compositions include several chemicals such as solvents or surfactants that are used to hold active ingredients in the composition. The topical composition of the invention can be used to hold or solubilize active ingredients without the use of the solvents or other components required by certain commercially available topical compositions.

The topical composition use solution according to the invention can be provided in numerous applications. The composition can be provided as a skin care product which is often used to administer vitamins, aloe, herbs, and drugs to skin tissue. Exemplary vitamins that are often delivered include vitamin A, vitamin E, and retinoic acid. Additionally, essential fatty acids such as borage oil and herbs such as aloe vera and evening primrose can be incorporated into the composition.

The topical composition can be used as a cosmetic composition. Exemplary cosmetic compositions according to the invention include lip care products such as lipstick and lip gloss, eye care products, skin care products, fragrances, botanicals, oils, herbs, baby products, bath products, soaps, pigments, scents, alcohols, flavors, aloe, glycerin, powders, nail polish, and foundation.

The topical composition can be used as a barrier composition to provide a barrier layer between skin tissue and the external environment.

The composition according to the invention can be provided as over the counter products or prescription products. Exemplary over the counter products include sunscreens, sun blocks, insect repellants, wound care products, burn care products, sunless tanning products, antifungal products, antibacterial products, antiviral products, acne prevention products, bath products, vitamins, minerals, deodorants, and anti-perspirants. The over the counter products can include drugs and/or pharmaceuticals. Prescription products can include peptides, metals, and/or drugs for skin disorders.

The composition according to the invention can be used as a hair care product, an animal care products, and a home care product. Exemplary hair care products according to the invention include shampoos, conditioners, mousses, stylers, finishers, dyes, and hair sprays. Exemplary animal care products include soaps, hair shampoo, hair conditioners, flea and tick baths, and prescription drugs for skin diseases. Exemplary home care products include towelettes, disinfectants, soaps, and cleaners.

The composition according to the invention can be used to provide an autocare product. Exemplary autocare products according to the invention include fabrics, leathers, vinyls, paints, metals, chromes, rubber, tires, and window treatments.

EXAMPLES

The following examples were carried out in order to demonstrate certain teachings of the invention. It should be understood that the invention is not limited to the examples of this application.

Example 1

Polyacrylic acid having less than 1% cross linking with a weight average molecular weight of between 400,000 and 500,000 and maleic acid/methylvinylether copolymer (MMVE) with a weight average molecular weight of 1,980,000 were used. For simplicity and ease of handling due to lower solution viscosities, the majority of work was performed using MMVE. The acidic polymers were easier to study by simple pH titrations of free —COOH groups. When increasing concentrations of PVPE up to 10% were mixed with MMVE or PA under anhydrous conditions at temperatures of 75° C. to 125° C., translucent, amber, waxy solids or liquids of high viscosity resulted. When heated in water to 65° C. and polymer concentrations of 10–15% suspensions were obtained that could then be titrated with normal KOH. Results are shown in FIG. 1. Mixtures of MMVE and PVPH prepared in the same way gave the results shown in FIG. 2.

Figure 2:
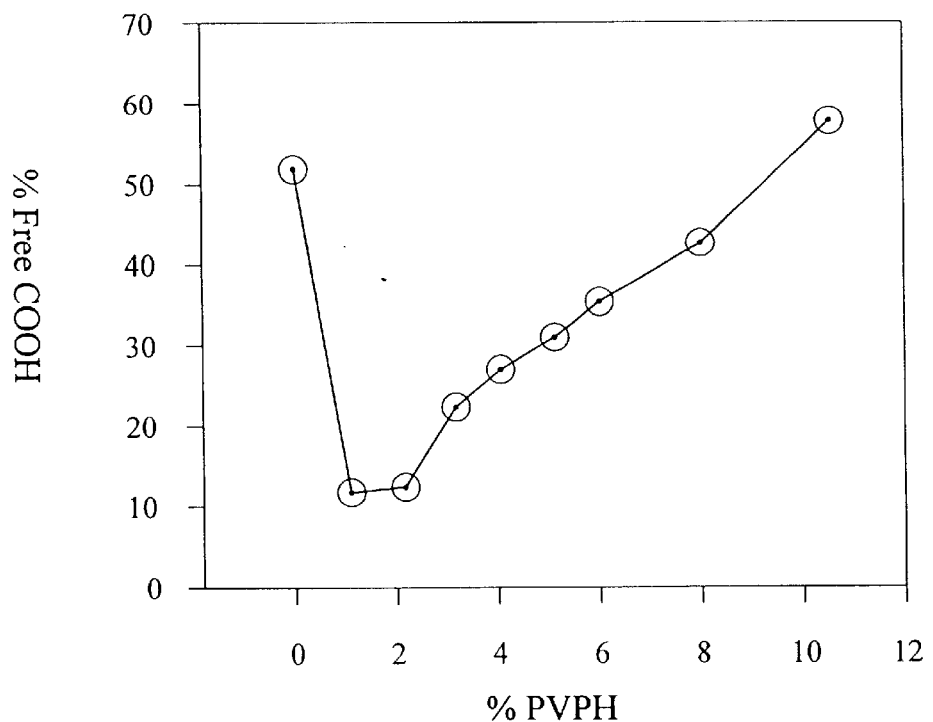
FIG. 2 is a graph showing percent free COOH of MMVE as a function of percent PVPH added.

FIGS. 1 and 2 show MMVE without any added PVPE or PVPH has only 50% of the —COOH groups titratable by KOH. Many Organic Chemistry textbooks use the following structure to describe the hydrogen bonding interactions of carboxylic acids.

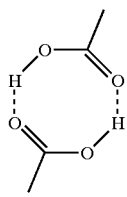

For low formula weight carboxylic acids, the hydrogen bonding interactions are considered weak ones in the area of 5 kcal/mole. With polymers having hundreds of —COOH groups per molecule and the added complexity of inter-chain as well as intra-chain interactions, these types of structures are likely quite stable and would require large energy input to disrupt them. Steric factors likely contribute additional stabilizing factors.

Figure 3:
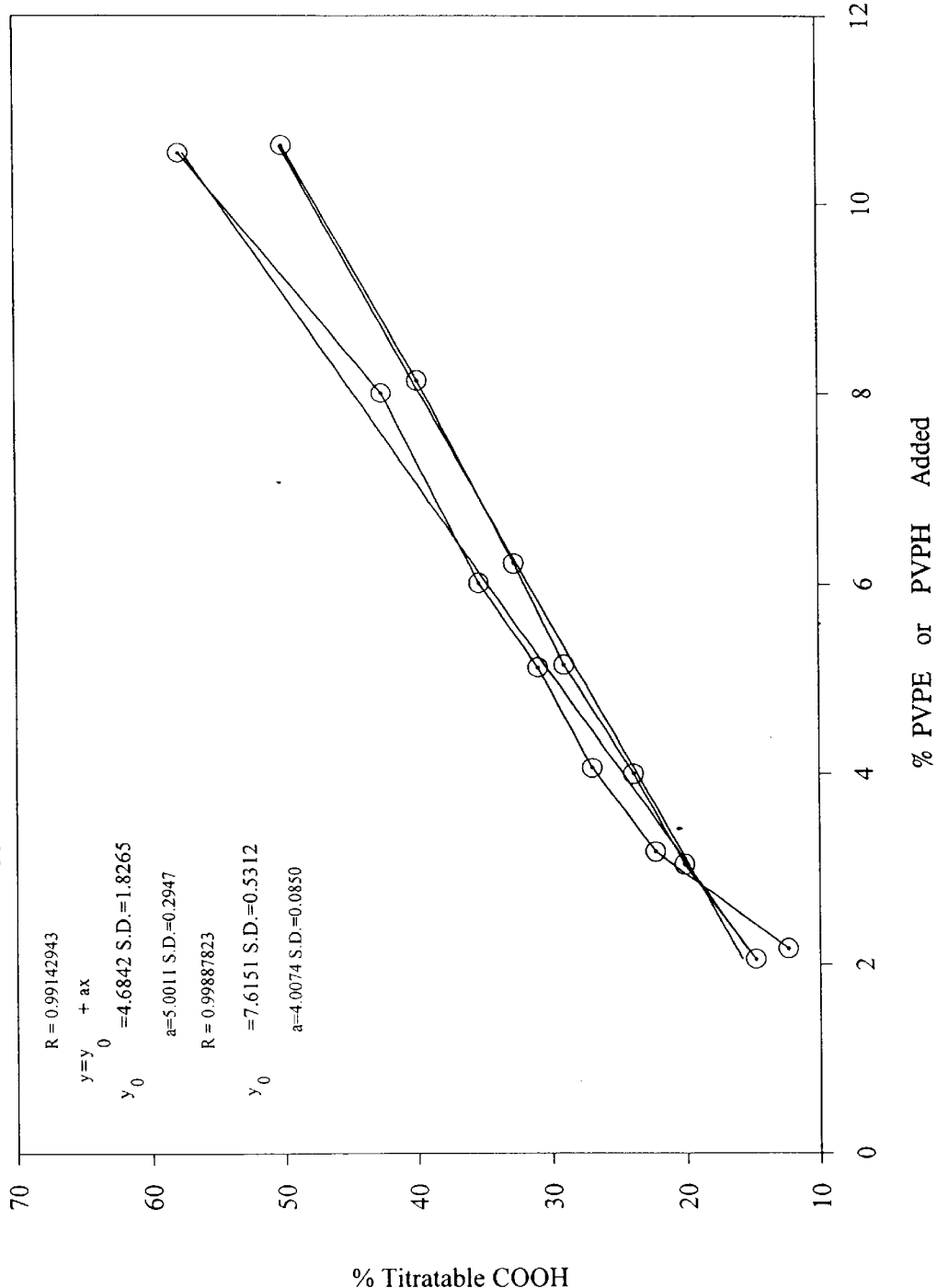
FIG. 3 is a graph of percent titratable COOH groups of MMVE as a function of percent PVPE or PVPH added.

FIGS. 1 and 2 also show that MMVE hydrogen bond structure is extensively disrupted by the addition of as little as 1% PVPE or PVPH. Adding more PVPE or PVPH results in the disappearance of —COOH groups. As seen in FIG. 3, the disappearance of —COOH groups is linear to slightly sinusoidal between 2 and 10% PVPE or PVPH.

Figure 4:
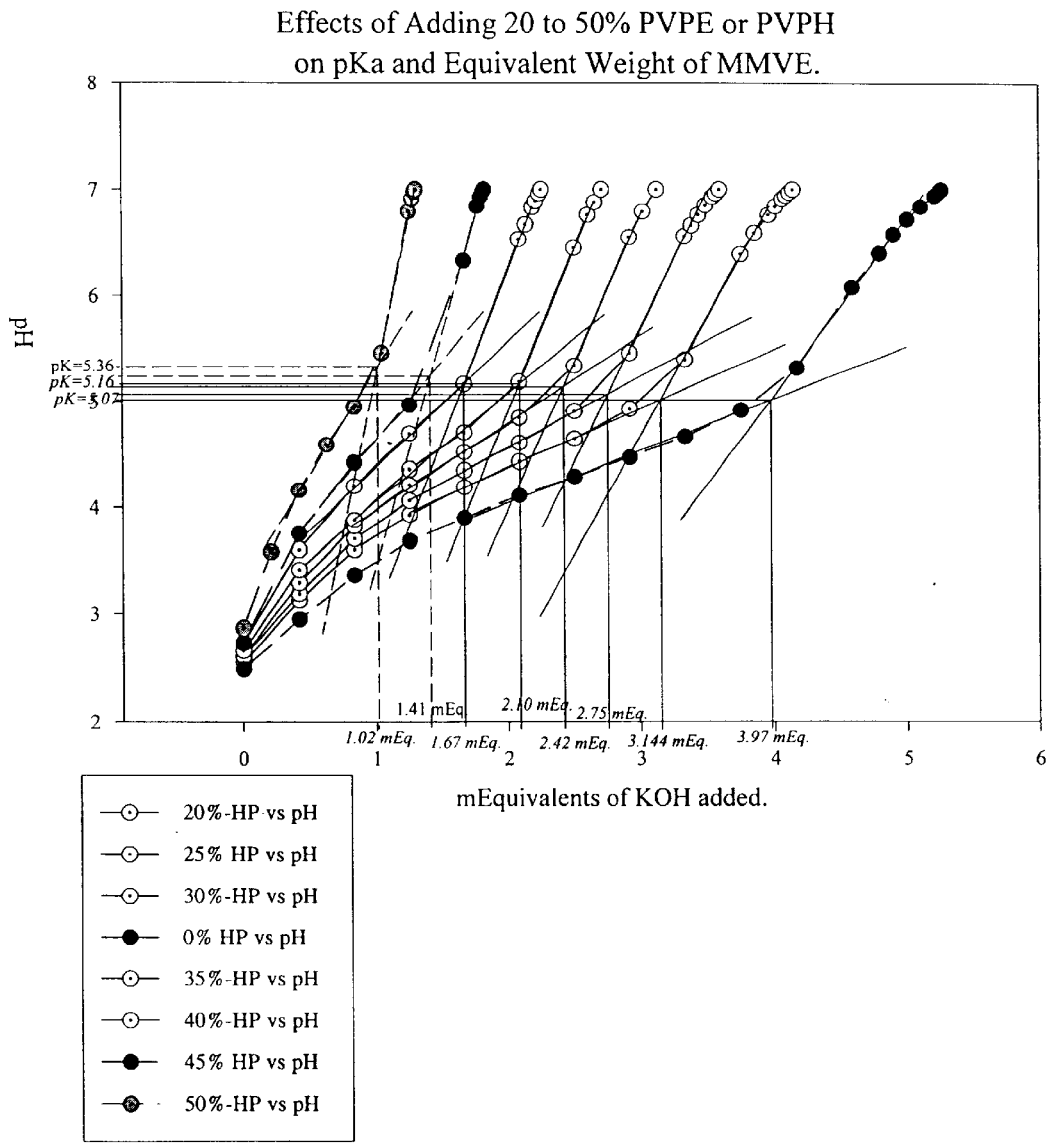
FIG. 4 is a graph showing the effects of adding 20 to 50 wt. % PVPE or PVPH on pKa and equivalent weight of MMVE.

FIG. 4 shows the effects on MMVE titration curves with the addition of 20–50% PVPE or PVPH. The intention here is to maximize skin binding (hydrophobic character) without extensive loss of water solubility (hydrophilic character).

In the legend to FIG. 4 "HP" refers to "Hydrophobic Polymers" as the data applies to PVPE and PVPH equally. FIG. 4 shows that while the "pKa" of MMVE changes slightly from 5 to 5.36, the mEqs. of Normal KOH required to reach the pKa is reduced by 75%, meaning that the number of titratable —COOH groups also has been reduced and the Equivalent Weight of MMVE has increased. Clearly there is an interaction between the —COOH groups of MMVE and PVPE and/or PVPH. It is difficult to perceive this interaction occurring between the $C_{16}$ and/or $C_{20}$ aliphatic side-chains of PVPH and PVPE. We believe the pyrrolidone ring shown below is responsible for this interaction.

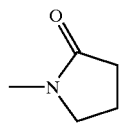

This is the structure of N-methylpyrrolidone, which has the same covalent structure as the pyrrolidone rings in PVPE and PVPH. The pyrrolidone ring is chemically very stable, yet it has a carbonyl oxygen that is electronegative and the amide nitrogen has a free pair of electrons, which can participate in resonance.

We believe the following structure explains the simplest form of a non-covalent complex between PA or MMVE and PVPE and/or PVPH.

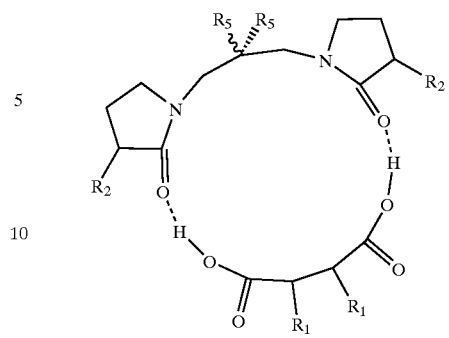

$R_2 = C_{16}H_{33}$ or $C_{20}H_{41}$
$R_1 = [C_5H_{11}O_5]_n$ or $[C_3H_6O_2]_n$
$R_5 = [C_{22}H_{41}NO]_n$

We realize that this complex as presented here is a simplistic form and may not exist at all primarily from steric considerations. The complex may not involve adjacent —COOH groups or pyrrolidone rings. The actual complex most likely involves intra-chain and inter-chain interactions, resulting in a three dimensional structure far too complex to present.

Example 2

Figure 5:
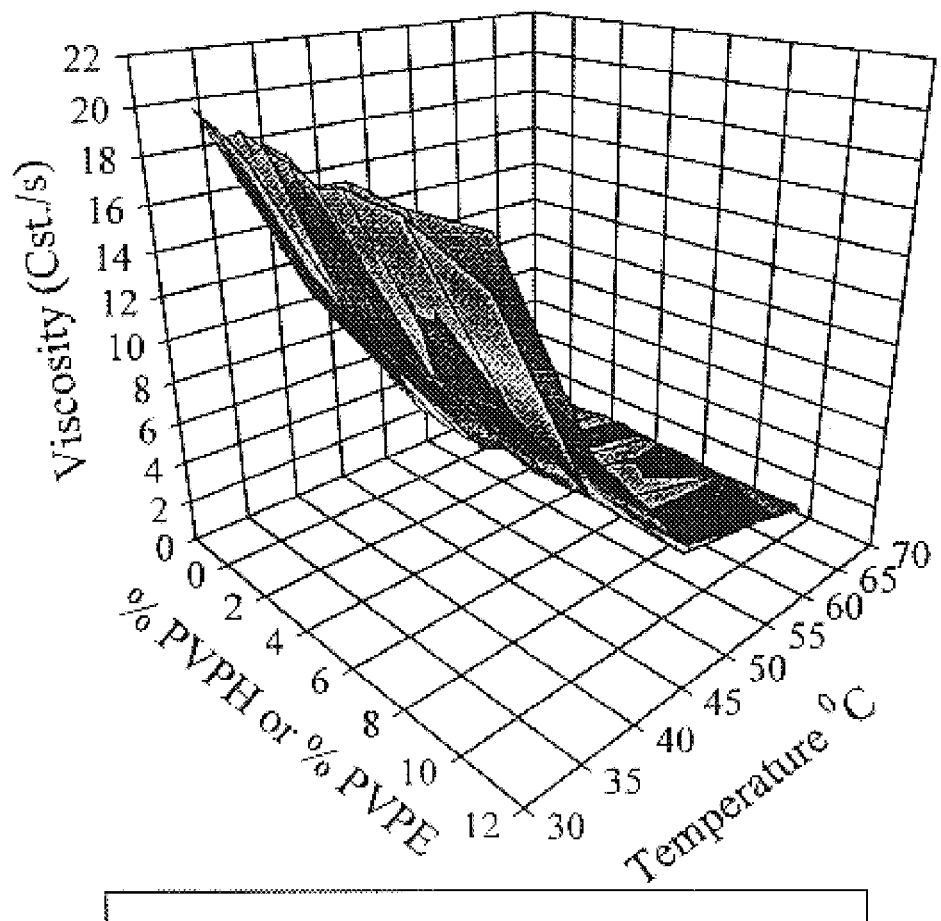
FIG. 5 is a graph showing MMVE solution viscosity as a function of percent PVPH or percent PVPE added and temperature.

Another tool for studying polymers is viscosity. We hoped to learn more information about the complexes by looking at viscosity measurements at variable concentrations of PVPE and PVPH and also as a function of temperature. FIG. 5 shows the results of these studies at a polymer concentration of 100 mg/ml. in water, and PVPE or PVPH concentrations of 0 to 10% at a pH of 8.0, and over the temperature range of 32° C. to 65° C.

The surfaces of these plots are remarkably similar with a few exceptions. At 2%, PVPE (blue surface) increases while PVPH (yellow surface) decreases. This decrease in viscosity recurs between 6% and 10% concentrations, and persists up to 50° C. Attempts were made to extend the study to lower total polymer concentrations (<100 mg/ml). This resulted in the complex dissociating at ~10 mg/ml and completely collapsing to starting materials at 5 mg/ml. PVPH was more prone to this dissociation than PVPE.

Since complex formation appears essentially the same with either PVPH or PVPE, we decided to look at complexes formed with a mixture of PVPH and PVPE. A molar ratio of 1:1 was chosen to begin the studies. Viscosity data for this mixture is shown in FIG. 6.

Figure 6:
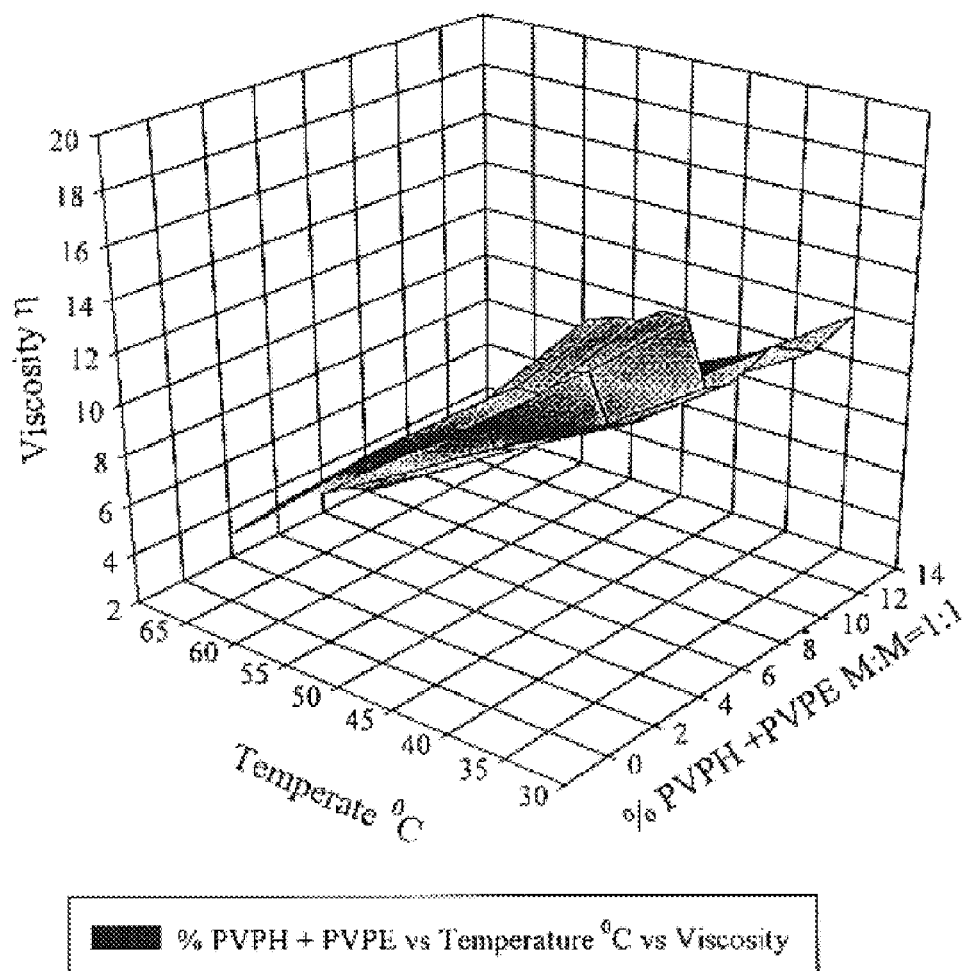
FIG. 6 is a graph showing MMVE viscosity as a function of temperature and percent of PVPH and PVPE.

Comparison of FIG. 5 with FIG. 6 shows that the drop in viscosity from 6–10% concentration of PVPH+PVPE is greater than with PVPH alone, and the slope of the surface as a function of temperature is less with the PVPH+PVPE mixture than with either PVPH or PVPE alone. This interaction between PVPH and PVPE was unexpected.

It is believed that two types of phase separations occur with the polymer complexes. The first is an upper phase of opaque, white material. This is the result of insolubility of the complex. The second is an upper layer of clear oily droplets or a waxy solid. This is the result of complex decomposition.

Example 3

Since the polymer composition according to the invention is designed to bind to the skin with resistance to wash-off, we developed a simple and rapid, gravimetric method to mimic skin application of the polymer system. This test utilizes hydrophilic nylon membranes normally used for solvent filtration. It is expected that these membranes possess mixed hydrophilic and hydrophobic properties similar to skin.

The membranes are weighed to the nearest 0.1 mg. The pre-weighed membranes are floated on a suspension of the test polymer solution and weighed to obtain the wet weight of sample applied. The membranes with test polymer are dried at 32–35° C. (skin temperature) for 30 minutes, and a dry weight is obtained. The dried membranes may then be soaked in water or a variety of solvents, re-dried and weighed a final time to yield the mg or % of polymer remaining on the membrane after treatment. It is expected that results on skin will be better.

Figure 7:
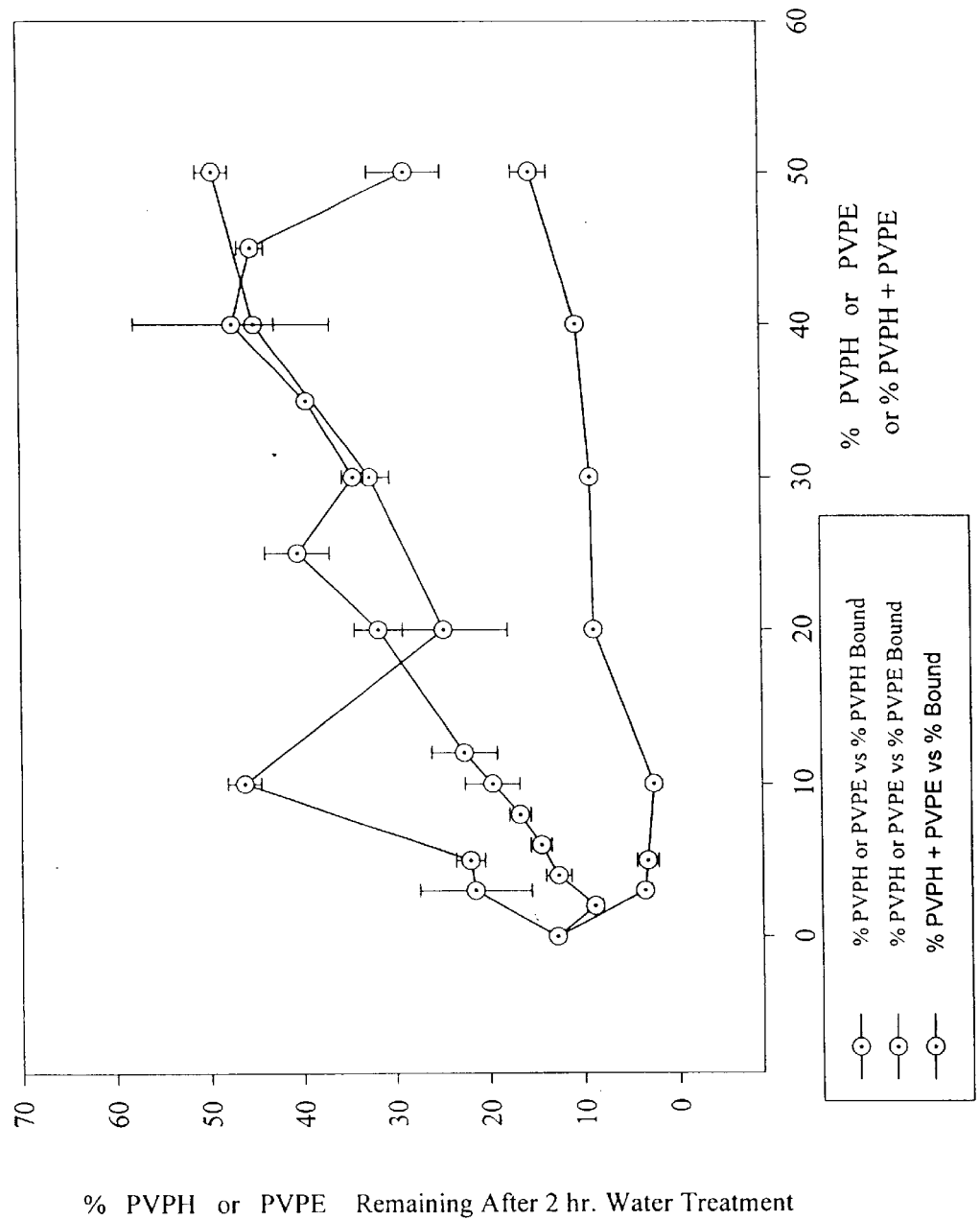
FIG. 7 is a graph showing the percent of polymer remaining bound to hydrophilic nylon membranes as a function of increasing percentage of PVPH or PVPE polymer.
Figure 8:
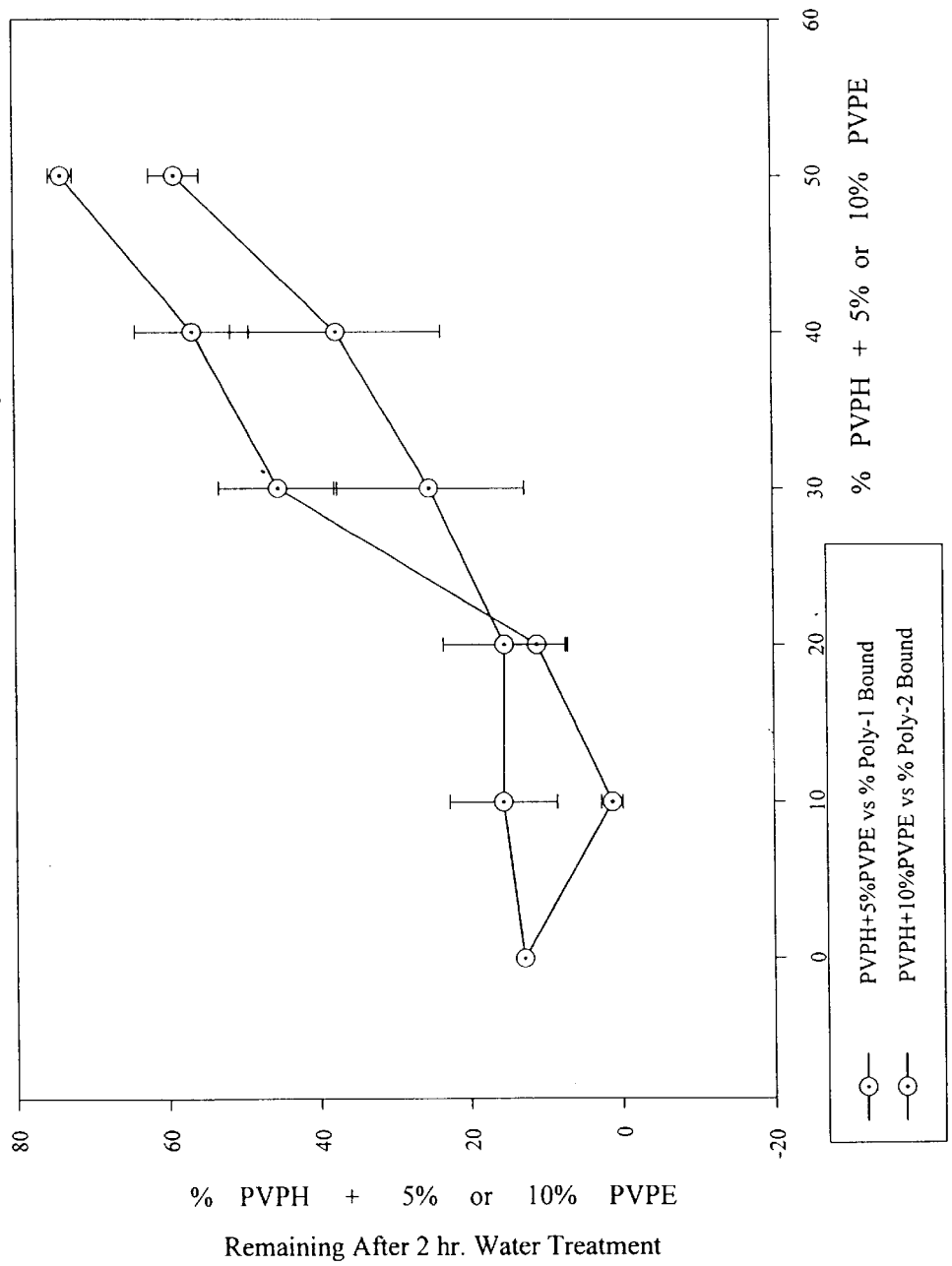
FIG. 8 is a graph showing the percent of polymer remaining bound to hydrophilic nylon membranes as a function of increasing percentage of PVPH+5 wt. % or 10 wt. % PVPE polymer.
Figure 9:
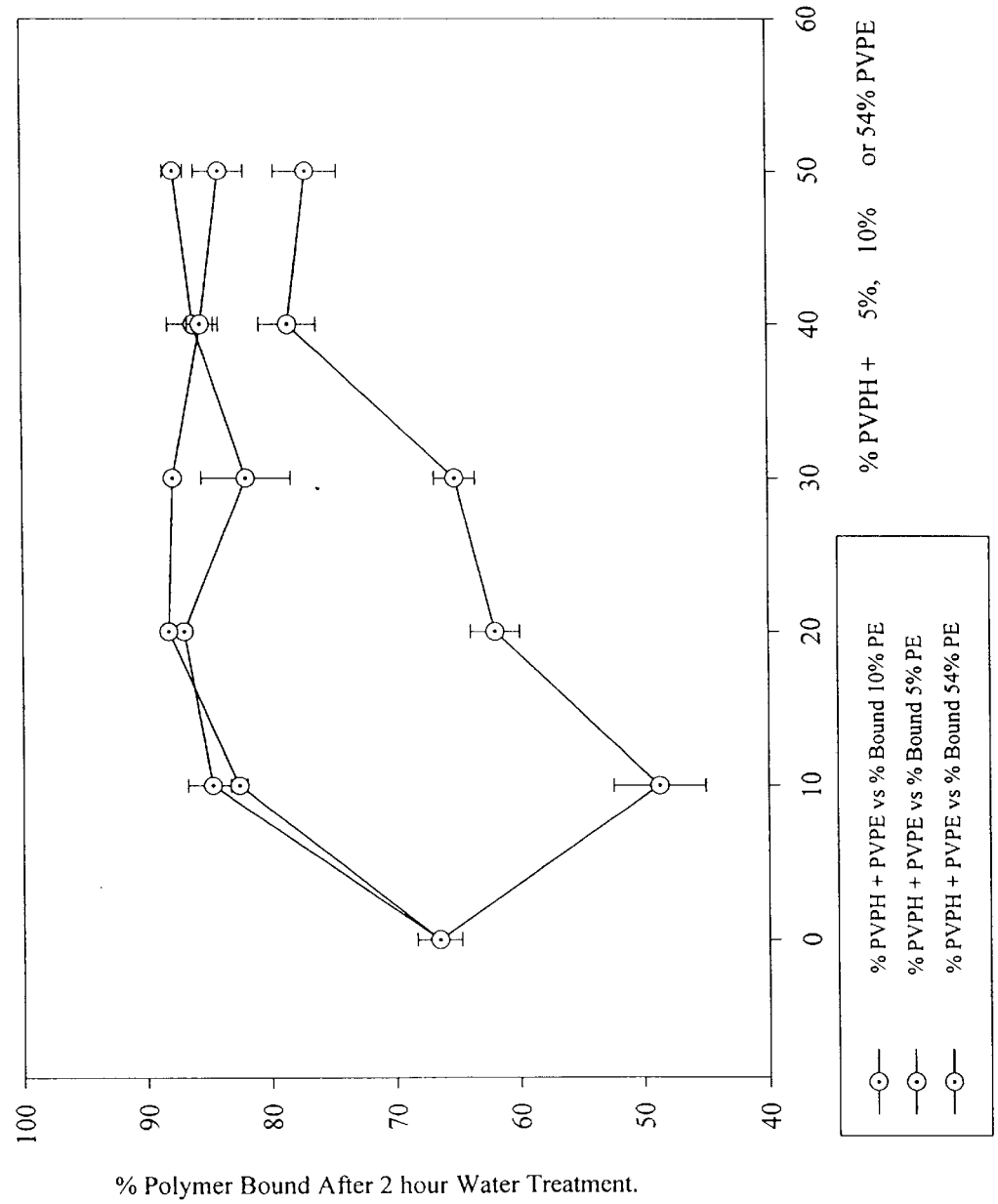
FIG. 9 is a graph showing the percent of starch-polymer complex bound as a function of percent PVPH at 5 wt. %, 10 wt. %, and 54 wt. % PVPE.
Figure 10:
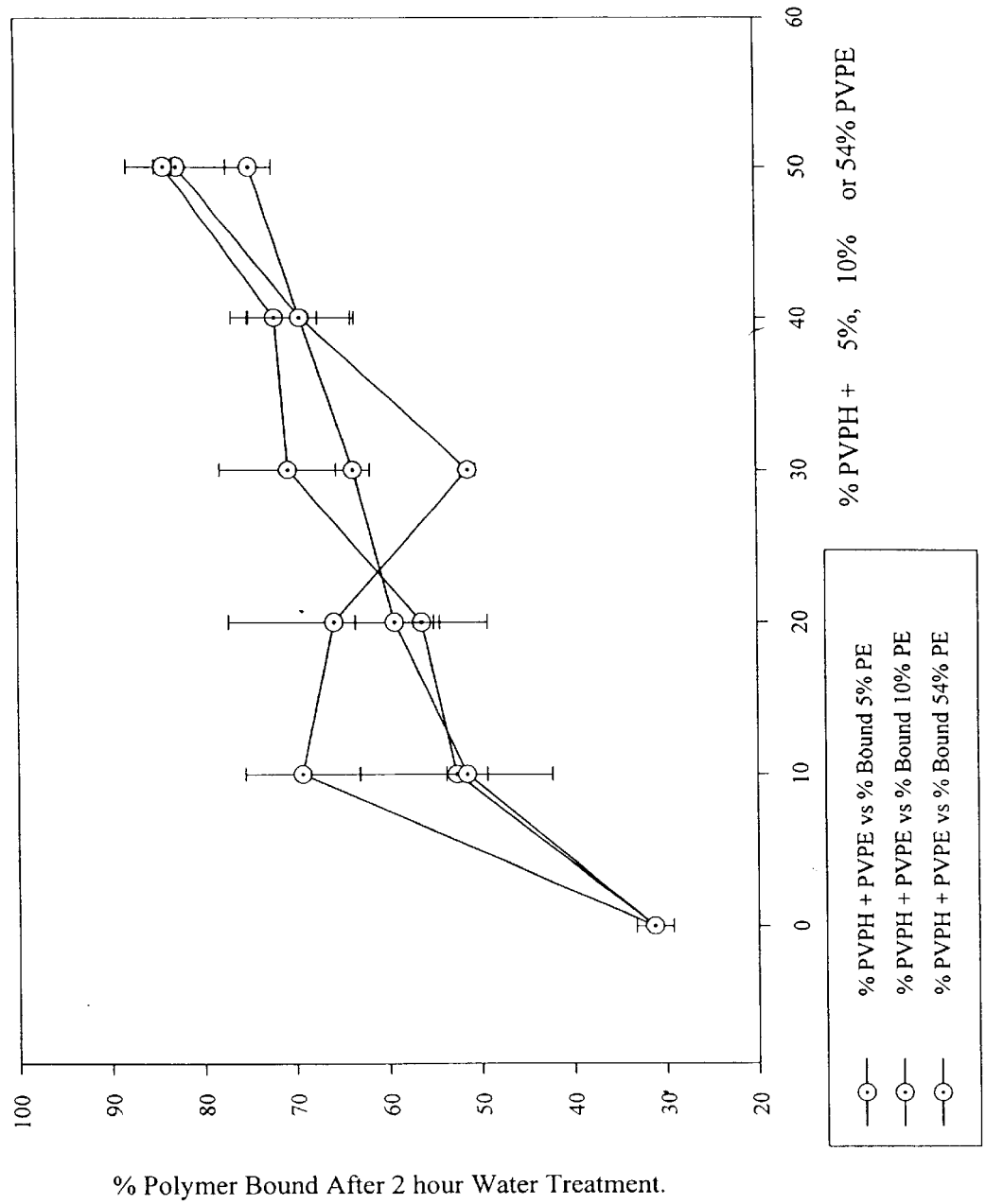
FIG. 10 is a graph showing the percent of PVOH-polymer complex bound as a function of percent PVPH at 5 wt. %, 10 wt. %, and 54 wt. % PVPE.

FIG. 7 shows the results of our binding study with MMVE complexes of PVPH, PVPE and a 1:1 molar ratio of PVPH+PVPE.

Error bars indicate standard deviation of the mean. The expected results were that PVPE+PVPH>=PVPE>PVPH, reasoning that the $C_{20}$ side chain of PVPE should adhere better than the shorter $C_{16}$ side chain of PVPH. However, the data clearly show that the complex of MMVE: PVPE is much more soluble in water than the complexes of MMVE: PVPH or MMVE: PVPH+PVPE. The high binding point at 10% PVPH is also tantalizing, however, complexes containing 10% hydrophobic polymer or less decompose to two phases in water within 24 hours of preparation. The MMVE: PVPH+PVPE curve hints that a cooperative interaction between PVPH and PVPE may be beneficial, but at lower molar ratios than 1:1. Similar studies were conducted with PVPH: PVPE ratios of 10:1 and 22:1. These data are shown in FIG. 8.

FIG. 8 clearly shows the synergism between PVPE and PVPH. Either PVPH: PVPE mixture 10:1 M (10%) or the 22:1 M (5%) result in 15–25% greater binding to the membranes than seen by either hydrophobic polymer alone or the 1:1 M ratio of the two. FIG. 8 also shows that a mixture of 95% PVPH+5% PVPE and 50% MMVE-$H_2O$ yields a product that 75% remains bound to the membranes after two hours of immersion in water. Similar binding data demonstrated the PA–PVPE+PVPH system was substantially the same (data not shown). At this point we considered the acidic hydrophilic and PVPE+PVPH system optimized.

Implied by the non-covalent structure is an equilibrium process for complex formation. The reversible nature of the complex by dilution also implies an equilibrium complex. Calculation of the ratio of pyrrolidone groups of PVPH+PVPE to —COOH groups of MMVE for the optimized, hydrated complex described above gives a value of 2.29:1. Because of the nature of the proposed complex, this value seems low. Complicating the issue is the fact that the complexes form emulsions, implying the complexes are not truly in solution, but are merely a suspension of micelles. This line of reasoning leads to the conclusion that the factors controlling the equilibrium (or rather equilibria, there are likely many) are not primarily involved with the aqueous phase. This conclusion accounts for the high stability of what may be thought of as a labile complex.

The MMVE and PA polymer complexes described to this point require the neutralization of —COOH groups for water solubility. This necessarily limits the useful pH range to 6–9 for formulation. It is expected that similar complexes should also form with hydrophilic polymers containing —OH groups instead of —COOH groups.

There are thousands of naturally occurring and man-made polymers with abundant —OH groups. Among these are starch, cellulose, derivatives of starch, derivatives of cellulose, carboxymethyl cellulose, polyvinyl alcohol, cyclodextrins, and dextrans. There is also the possibility that polyvinylpyrrolidone (Povidone) may also interact with PVPH+PVPE.

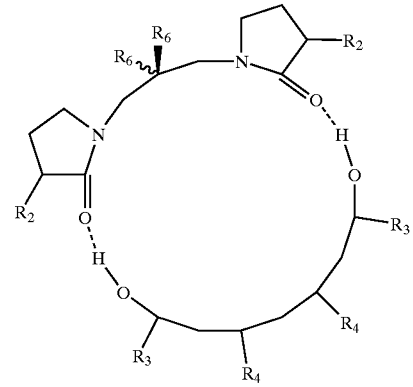

$R_3 = [C_6H_{11}O_6]_n$ or $[C_{28}H_{42}O_{25}]_n$ or $[C_{25}H_{40}N_4O_4]_n$
$R_4 = OH$
$R_6 = [C_{26}H_{49}NO]_n$

All of the above compounds formed complexes with PVPE: PVPH mixtures under anhydrous conditions at temperatures between 80–110° C. The complexes were clear to translucent amber solids or high viscosity liquids. Hydration of these complexes to a total of 40–46% water at 65° C., produced hard, white to off-white, granular or waxy solids. Further dilution to working solutions of 10–15% polymer required the addition of 0.5–10% surfactant (most often 9 to 10 mole nonylphenolethoxylates) to achieve stable emulsions.

In an attempt to overcome the difficulty of forming stable, aqueous emulsions, we dissolved the hydrophilic polymers in water at concentrations of 11–17%, depending on the polymer's solubility then added PVPE: PVPH mixtures to final concentrations of 46–51% and heated to 80–95° C. These reactions produced materials indistinguishable from the products formed under anhydrous conditions and hydrated post-synthesis.

As the —OH group polymers offer no easily analyzable groups as we had with MMVE and PA polymers above, we began looking at binding data. The results for starch are shown in FIG. 9.

Unlike the MMVE polymer complex, 5 or 10% PVPE showed very little difference in binding. Binding appears maximized at 10–20% PVPH+5 or 10% PVPE.

However, significant decomposition (see Note above) of the complex occurred at 10 and 20% PVPH+5 or 10% PVPE. The lowest stable concentration was 30% PVPH+PVPE at all levels of PVPE, and the most stable aqueous emulsion paradoxically was at 40% PVPH+54% PVPE (1:1 M).

Results with polymer complexes utilizing polyvinylalcohol (PVOH) as the hydrophilic portion are shown in FIG. 10.

Carboxymethylcellulose (CMC), like PA mentioned above, is commercially used as a viscosity builder for aqueous solutions. A 1% solution of CMC has a viscosity of ~2,000 Csts/s. A 1% solution of PA at neutral pH has a viscosity of >4,000 Csts/s. At acidic pH, a 1% solution of PA has a viscosity of ~250 Csts/s. Neutralization of the —COOH groups on PA causes the increase in viscosity. CMC requires no such neutralization as the —COOH groups are tied up as methyl esters.

Complex formation of CMC and PA with PVPH+PVPE mixtures gives drastically different results. Complexes of PA under anhydrous conditions at 90 to 125° C. and subsequent hydration to a 40% water content, yields solutions or gels of extremely high viscosity, as if the —COOH groups have been neutralized, or are unavailable for titration as seen with MMVE. Subsequent dilution of these gels to 0.68% PA content, results in solutions of ~5500 Csts/s. This is a considerable increase in viscosity over PA alone.

Complex formation with CMC under similar conditions results in a substantial decrease in solution viscosity. PVPH+PVPE content in excess of 30% and dilution to a 1% concentration of CMC gives a solution viscosity of ~800 Csts/s.

Figure 11:
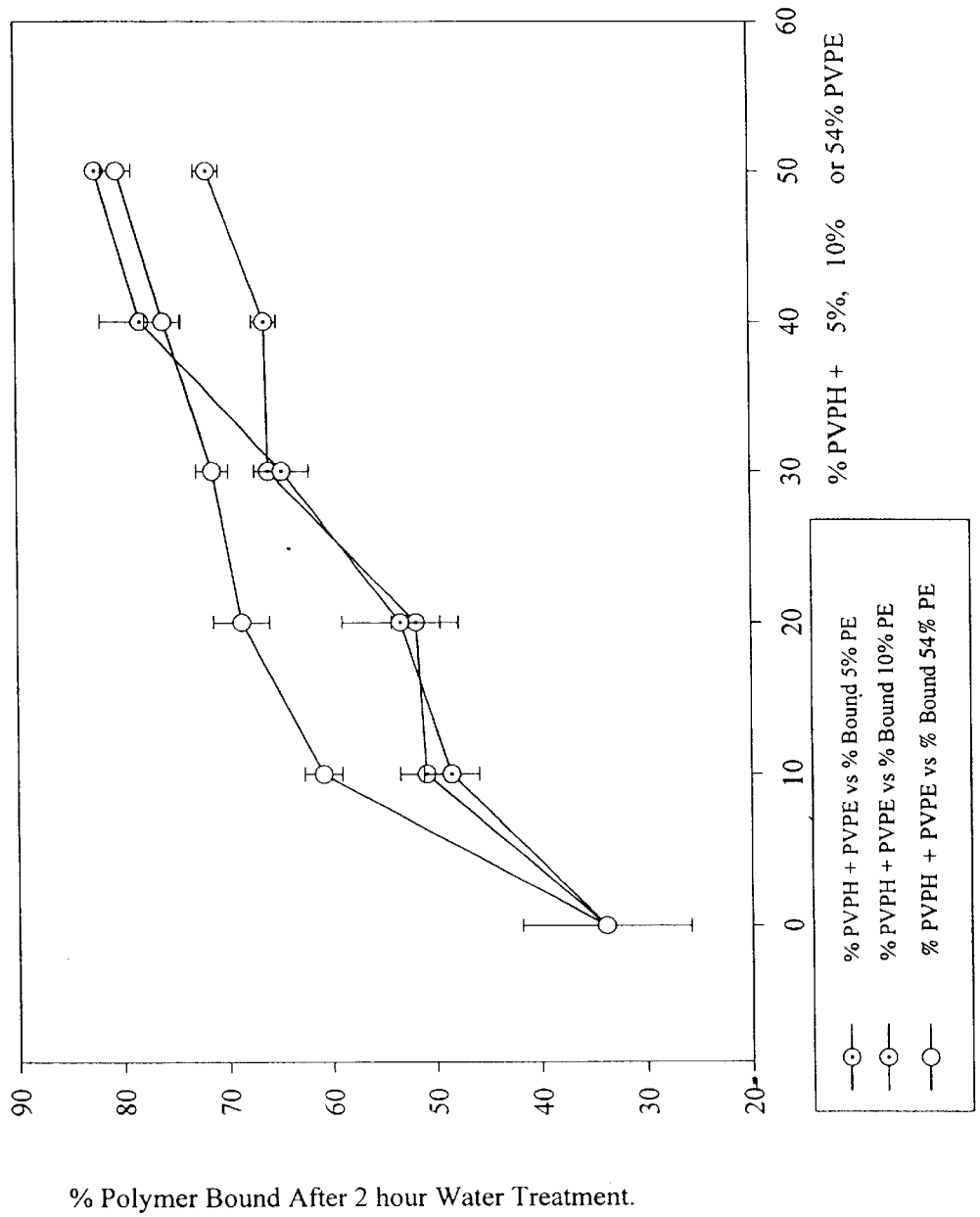
FIG. 11 is a graph showing the percent of CM-cellulose-polymer complex bound as a function of percent PVPH at 5 wt. %, 10 wt. %, and 54 wt. % PVPE.

Although the complexes formed with CMC and PA are believed to be similar as shown in FIGS. 11 and 17, the results of the complex formation have drastically different effects on CMC and PA ability to increase solution viscosity.

Results of the membrane binding studies with the CMC PVPH+PVPE complexes are shown in FIG. 11.

FIG. 11 shows that the CMC-PVPH+54% PVPE yields a higher degree of binding at all concentrations of PVPH+PVPE. At 40% PVPE+PVPH the 10% PVPE mixture is equivalent to the 54% PVPE mixture.

Cyclodextrins offer an interesting opportunity. Cyclodextrins are used as encapsulants in the food, cosmetic and pharmaceutical industry. They are cyclic oligosaccharides having 5 to 8 sugar residues with cavities in their centers. These cavities accommodate a wide variety of "guest" molecules that form stable complexes. The "guest" molecules may then be released under controlled conditions. Formation of guest complexes can also stabilize molecules that are volatile or decompose in water. A preferred cyclodextrin that can be used according to the invention is β-cyclodextrin having seven glucose residues and has a central cavity 6.5 Å in diameter and a formula weight of 1135. A representation of this material is provided below.

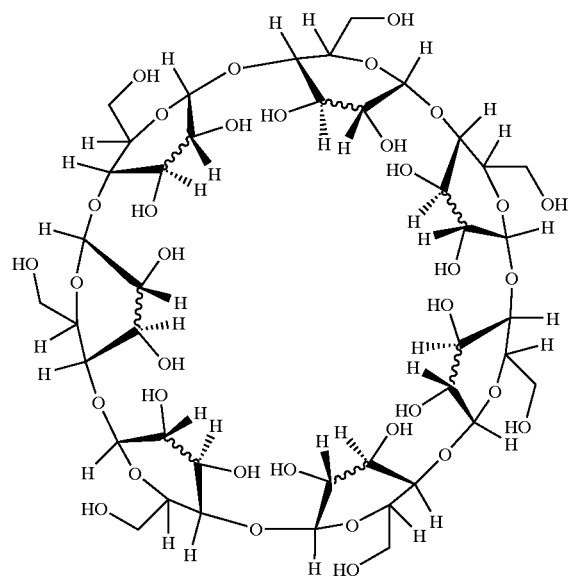

Each glucose residue has 3 —OH groups (similar to Starch and CMC) that offer an opportunity for complex formation with PVPH+PVPE. It is desirable to produce a polymer complex that is capable of encapsulating a variety of active agents that will also bind tightly to hydrophobic substrates such as skin. Cyclodextrins are too water soluble to bind to the skin for any appreciable time, particularly if the skin is subsequently exposed to water.

Figure 12:
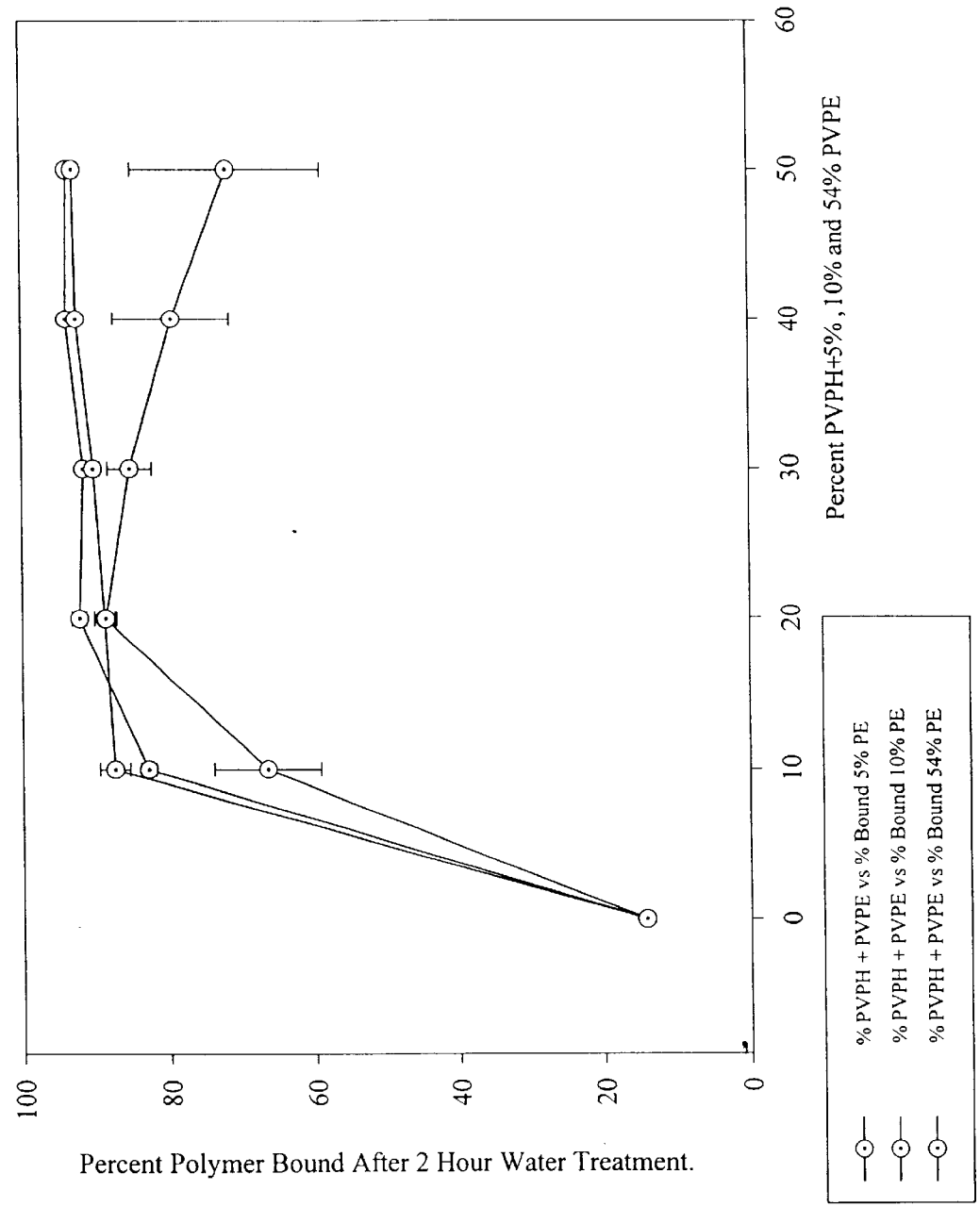
FIG. 12 is a graph showing the percent of cyclodextrin PVPH and PVPE polymer complex bound at 5 wt. %, 10 wt. %, and 54 wt. % PVPE.

Most of the complexes with PVPH+PVPE shown in FIG. 12 lack any appreciable solubility in water, a property that has been characteristic of all other polymer complexes. The notable exceptions are 10 and 20% PVPH+54% PVPE, which are completely soluble in water (pyrrolidone:—OH ratios of 0.4 and 0.8 respectively). Since the cavity in the β-cyclodextrin is known to be hydrophobic, and the water solubility of the guest effects the water solubility of the cyclodextrin complex, it is possible that PVPH and/or PVPE have occupied the cavity as a Guest molecule. In addition, β-cyclodextrin is a relatively small molecule with all of its —OH groups lying on the outside of the molecule. If all of the —OH groups formed complexes with pyrrolidone groups, none would be available to promote water solubility. All of the complexes shown in FIG. 12, with the exceptions noted above, are soluble in nonpolar solvents. This accounts for the >90% binding of the majority of complexes in FIG. 12.

Closely related are the dextrans. Dextran is an oligosaccharide of glucose residues held together with α-1,6 glycosidic linkages much like starch. Dextrans lack the α-1,4 glycosidic linkages seen in amylopectin. Each glucose residue contains 3 —OH groups to complex with PVPH+PVPE. Dextrans are used commercially as fillers, thickeners and wetting agents. A preferred dextran according to the invention is Dextran-70 having a weight average molecular weight of 70,000 and a range of 60–90,000 (Low Fraction).

Figure 13:
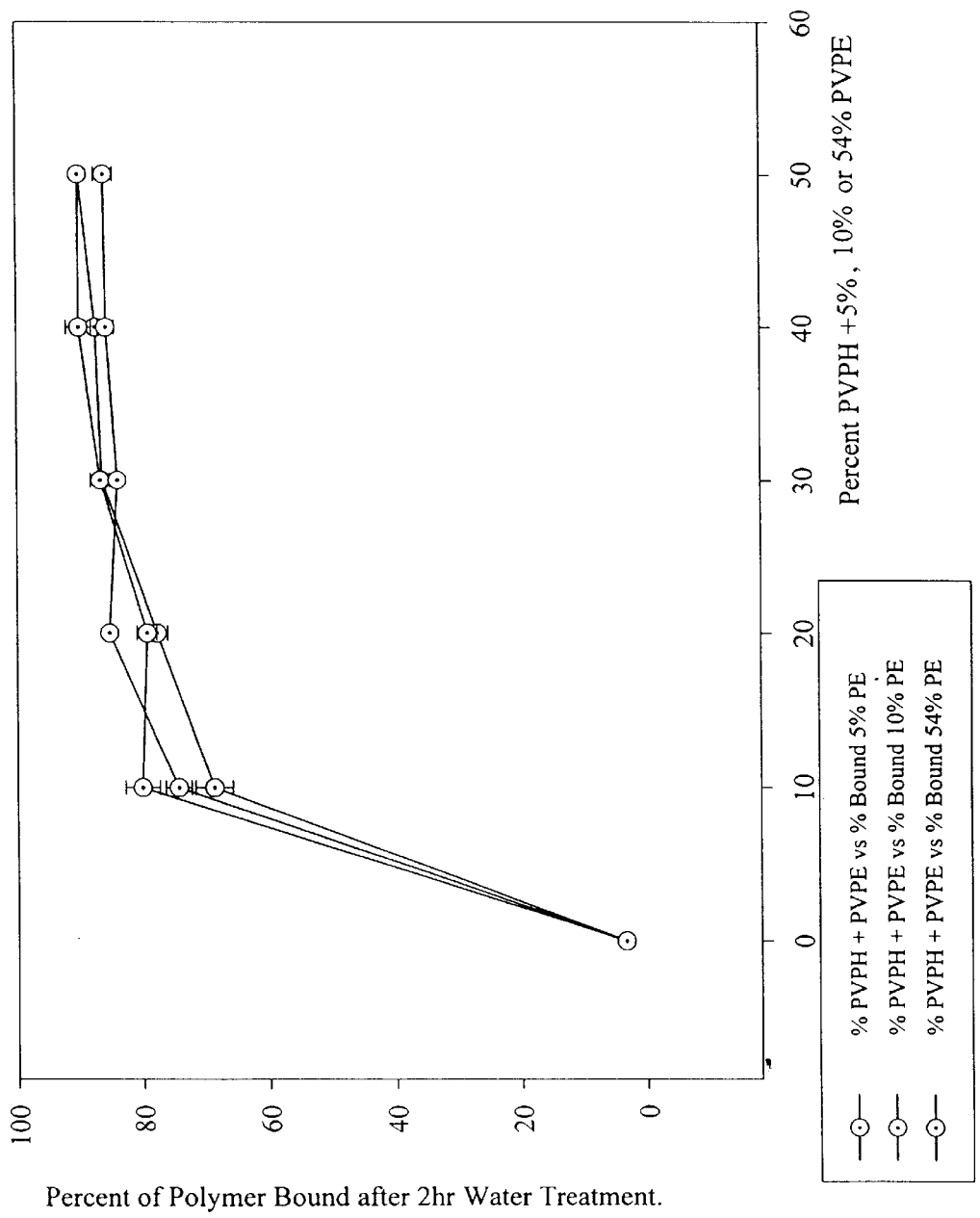
FIG. 13 is a graph showing the percent of Dextran 70 polymer complex bound as a function of percent PVPH at 5 wt. %, 10 wt. %, and 54 wt. % PVPE.

Dextran-70 is extremely soluble in water. It was anticipated that high levels of PVPH+PVPE would be required to achieve the water resistant binding we desired. This was not the case as seen in FIG. 13. Binding rose sharply from 3% for the Dextran alone to nearly 80% with the addition of 10% PVPH+PVPE. Binding remained nearly constant over the range of PVPH+PVPE concentrations. All of the complexes formed stable emulsions.

Figure 14:
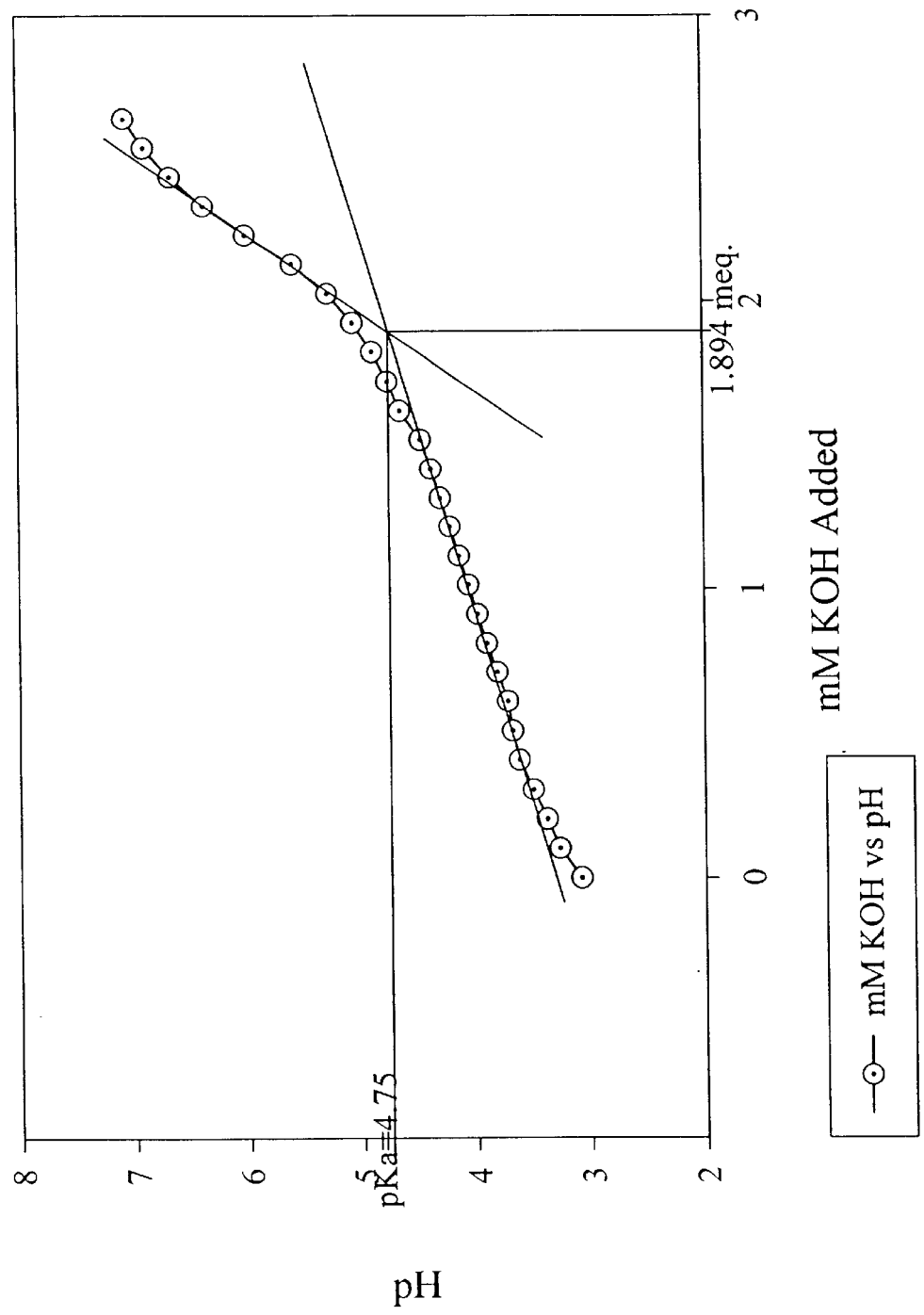
FIG. 14 is a graph showing the pKa for MMVE/PVP polymer complex.

Polyvinylpyrrolidone (PVP) forms sticky, yellow complexes with both PVPH+PVPE mixtures and hydrophilic polymers. Although quite water soluble itself, most of the complexes formed with PVP are highly insoluble in water. The complex formed between MMVE and PVP is a hard, transparent solid. This complex is soluble in water at a pH of 4.0 or higher. FIG. 14 shows the titration curve for MMVE/PVP produced at functional group parity ratio of 0.9 —COOH/pyrrolidone.

When FIG. 14 is compared to the native MMVE data presented in FIG. 4, calculation of the Equivalent Weight of MMVE is 168, which is nearly twice the expected value of 87, based on the composition of MMVE. This calculation indicates ~51% of the —COOH groups on MMVE are not available for titration. Calculation of the Equivalent Weight of the MMVE/PVP complex in FIG. 14, gives a value of 448, indicating ~19% of the —COOH are available for titration. Since PVP has no aliphatic side chains, the —COOH groups of MMVE must be tied up in a complex with the pyrrolidone rings as proposed in FIG. 11.

PVP is unique in our polymer complex system in that it can be substituted for either the hydrophobic polymers or the hydrophilic polymers and yet forms the same types of complexes. Complexes with PVPH+PVPE are soluble only in nonpolar solvents.

The PVP-PVPH+PVPE complex is soluble in ether-alcohol 75:25 or hexane. The PVP-CMC complex, formed in aqueous solution, retains extremely high viscosity and limited water solubility, requiring hydration levels in excess of 85% to obtain working viscosities. PVP-CMC dries to a hard, transparent, brittle film. Once dried, the film is difficult to hydrate.

The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A method for manufacturing a topical composition, the method comprising steps of:
   (a) melt processing a mixture to provide a topical composition precursor, the mixture comprising:
      (i) hydrophobic polymer composition comprising repeating pyrrolidone/alkylene groups, wherein the alkylene groups contain at least 10 carbon atoms;
      (ii) hydrophilic polymer composition comprising repeating carboxylic acid groups and/or repeating hydroxyl groups; and
      (iii) less than about 1 wt. % water; and
   (b) diluting the topical composition precursor to provide a water concentration of at least about 30 wt. % based on the weight of the topical composition.

2. A method according to claim 1, further comprising a step of:
   (a) adding at least one active ingredient to the topical composition, the active ingredient comprising at least one of antimicrobial agent, antifungal agent, anti-inflammatory agent, anti-viral agent, drugs, sunscreens, vitamins, α-hydroxy acids, surfactants, fragrances, pigments, and dyes.

3. A method according to claim 1, wherein the step of melt processing comprises mixing the hydrophobic polymer composition and the hydrophilic polymer composition at a temperature of greater than 50° C.

4. A method according to claim 1, wherein the step of melt processing comprises mixing the hydrophobic polymer composition and the hydrophilic polymer composition at a temperature of greater than 125° C.

5. A method according to claim 1, further comprising a step of:
   (a) diluting the topical composition precursor with water to provide a composition containing between about 30 wt. % and about 45 wt. % water based on the weight of the topical composition.

6. A method according to claim 5, further comprising a step of:
   (a) further diluting the topical composition in a separate step to provide a composition containing at least about 95 wt. % water based on the weight of the topical composition.

7. A method according to claim 1, further comprising a step of:
   (a) adding surfactant to the topical composition.

8. A method according to claim 7, wherein the surfactant comprises at least one of an ethoxylated surfactant, a propoxylated surfactant, an ethoxylated-propoxylated surfactant, and a mixture thereof.

9. A method according to claim 1, wherein the composition comprises between about 30 wt. % and about 45 wt. % water.

10. A method according to claim 1, wherein the composition comprises between about 3 wt. % and about 10 wt. % of the hydrophilic polymer composition and between about 30 wt. % and about 50 wt. % of the hydrophobic polymer composition.

11. A method according to claim 1, wherein the topical composition comprises between about 70 wt. % and about 96 wt. % water.

12. A method according to claim 1, wherein the hydrophobic polymer composition comprises a mixture of at least two different poly(vinylpyrrolidone/alkylene) polymers, wherein the alkylene group of each polymer contains at least about 10 carbon atoms.

13. A method according to claim 1, wherein the hydrophilic polymer composition comprises at least one of:
   (a) polyacrylic acid having a weight average molecular weight of at least about 50,000 and exhibiting less than 1% cross-linking;
   (b) poly(maleic acidlmethylvinylether) copolymer having a weight average molecular weight of at least about 50,000;
   (c) starch;
   (d) derivatives of starch;
   (e) cellulose;
   (f) derivatives of cellulose;
   (g) carboxymethyl cellulose;
   (h) polyvinyl alcohol;
   (i) cyclodextrins;
   (j) dextrans; and
   (k) mixtures thereof.

14. A method according to claim 1, wherein the hydrophilic polymer composition comprises polyacrylic acid having a weight average molecular weight of between about 50,000 and about 4,000,000 and exhibiting less than 1% cross-linking.

15. A method according to claim 1, wherein the hydrophilic polymer composition comprises poly(maleic acid/methylvinylether) copolymer having a weight average molecular weight of between about 50,000 and about 4,000,000.

16. A method according to claim 1, wherein the composition further comprises between about 0.5 wt. % and about 5 wt. % surfactant.

17. A method according to claim 16, wherein the surfactant comprises at least one of an ethoxylated surfactant, a propoxylated surfactant, an ethoxylated-propoxylated surfactant, and a mixture thereof.

18. A method for manufacturing a topical composition precursor comprising melt processing a mixture comprising:
   (a) hydrophobic polymer composition comprising poly(vinylpyrrolidone/alkylene) polymer, wherein the alkylene group contains at least about 10 carbon atoms;
   (b) hydrophilic polymer composition comprising at least one of:
      (i) polyacrylic acid having a weight average molecular weight of at least about 50,000 and exhibiting less than 1% cross-linking;
      (ii) poly(maleic acid/methylvinylether) copolymer having a weight average molecular weight of at least about 50,000;
      (iii) starch;
      (iv) derivatives of starch;
      (v) cellulose;
      (vi) derivatives of cellulose;
      (vii) carboxymethyl cellulose;
      (viii) polyvinyl alcohol;
      (ix) cyclodextrins;
      (x) dextrans;
      (xi) mixtures thereof; and (c) wherein the functional group parity of the hydrophobic polymer composition and the hydrophilic polymer composition is provided at a ratio of between about 1:1 and 5:1, and the topical composition precursor contains less than about 1 wt. % water.

19. A method according to claim 18, wherein the hydrophobic polymer composition comprises at least different poly(vinylpyrrolidone/alkylene) polymers, wherein the alkylene group of each polymer contains at least about 10 carbon atoms.

20. A method according to claim 19, wherein the at least two different poly(vinylpyrrolidone/alkylene) polymers comprises a first poly(vtnylpyrrolidone/alkylene) polymer and a second poly(vinylpyrrolidone/alkylene) polymer, wherein the first poly(vinylpyrrolidone/alkylene) polymer is provided at a concentration of between about 5 wt. % and about 54 wt. %, based on the weight of the hydrophobic polymer composition.

21. A method according to claim 18, wherein the hydrophilic polymer composition comprises polyacrylic acid having a weight average molecular weight of between about 50,000 and about 4,000,000.

22. A method according to claim 18, wherein the poly (maleic acid/methylvinylether) copolymer has a weight average molecular weight of between about 50,000 and 4,000,000.

23. A method according to claim 18, wherein the poly (vinylpyrrolidone/alkylene) polymer comprises poly (vinylpyrrolidone/1-eicosene).

24. A method according to claim 18, wherein the poly (vinylpyrrolidone/alkylene) polymer comprises poly (vinypyrrolidone/hexadecene).

25. A method according to claim 18, wherein the functional group parity of the hydrophobic polymer composition to the hydrophilic polymer composition is provided at a ratio of between about 1.5:1 and about 3:1.

26. A method according to claim 18, wherein the hydrophobic polymer composition is provided at a concentration of between about 72 wt. % and about 98 wt. %, and the hydrophilic polymer composition is provided at a concentration of between about 2 wt. % and about 25 wt. %, based on the weight of the topical composition precursor.

* * * * *